United States Patent
Schallek

(10) Patent No.: US 9,844,320 B2
(45) Date of Patent: Dec. 19, 2017

(54) SYSTEM AND METHOD FOR OBSERVING AN OBJECT IN A BLOOD VESSEL

(71) Applicant: Jesse Schallek, Rochester, NY (US)

(72) Inventor: Jesse Schallek, Rochester, NY (US)

(73) Assignee: University of Rochester, Rochester, NY (US)

( * ) Notice: Subject to any disclaimer, the term of this patent is extended or adjusted under 35 U.S.C. 154(b) by 124 days.

(21) Appl. No.: 14/602,480

(22) Filed: Jan. 22, 2015

(65) Prior Publication Data

US 2015/0208915 A1    Jul. 30, 2015

Related U.S. Application Data

(60) Provisional application No. 61/933,102, filed on Jan. 29, 2014.

(51) Int. Cl.
| | | |
|---|---|---|
| *A61B 3/00* | (2006.01) | |
| *A61B 3/14* | (2006.01) | |
| *A61B 3/12* | (2006.01) | |
| *A61B 3/10* | (2006.01) | |

(52) U.S. Cl.
CPC .............. *A61B 3/1241* (2013.01); *A61B 3/14* (2013.01); *A61B 3/102* (2013.01)

(58) Field of Classification Search
CPC ......... A61B 3/102; A61B 3/1241; A61B 3/14; A61B 3/113; A61B 3/1233; A61B 5/026; A61B 5/02007; A61B 5/14546; A61B 5/14551; A61B 5/7246; A61B 6/12; G06T 2207/30041; G06T 2207/10064; G06T 2207/10101; G06T 2207/10121; G06T 2207/30101; G06T 2207/30104

USPC ........ 351/205, 206, 210, 246; 600/310, 322, 600/427, 476, 504; 382/133
See application file for complete search history.

(56) References Cited

U.S. PATENT DOCUMENTS

| | | | | |
|---|---|---|---|---|
| 4,579,430 A | * | 4/1986 | Bille .................... | A61B 3/1015 351/206 |
| 5,394,199 A | * | 2/1995 | Flower ................. | A61B 3/1241 351/205 |

(Continued)

OTHER PUBLICATIONS

Zhangyi Zhong, Benno L. Petrig, Xiaofeng Qi, and Stephen A. Burns. In vivo measurement of erythrocyte velocity and retinal blood flow using adaptive optics scanning laser ophthalmoscopy. Opt Express. Aug. 18, 2008; 16(17): 12746-12756.*

(Continued)

*Primary Examiner* — Bumsuk Won
*Assistant Examiner* — Collin X Beatty
(74) *Attorney, Agent, or Firm* — Harris Beach PLLC

(57) ABSTRACT

A method for creating a virtual 2D image of an object moving in a blood vessel includes the steps of: providing an imaging apparatus capable of acquiring 1D images. The imaging apparatus is communicatively coupled to a computer. Multiple 1D images of a substantially fixed footprint on a surface of an organ are acquired over a period of time. A virtual 2D image showing the object moving in the blood vessel is formed by combining by computer the multiple 1D images. The virtual 2D image can be displayed and/or saved to a non-volatile memory. A system to perform the method is also described. Another method for creating a virtual 1D image of an object moving in a blood vessel is also described.

9 Claims, 22 Drawing Sheets

(56) References Cited

U.S. PATENT DOCUMENTS

| | | | | |
|---|---|---|---|---|
| 5,633,695 | A * | 5/1997 | Feke | A61B 3/1025 351/205 |
| 6,276,798 | B1 * | 8/2001 | Gil | A61B 5/0059 351/206 |
| 6,411,839 | B1 * | 6/2002 | Okinishi | A61B 3/0033 351/208 |
| 6,890,076 | B2 * | 5/2005 | Roorda | G01J 9/00 351/205 |
| 7,118,216 | B2 * | 10/2006 | Roorda | G01J 9/00 351/205 |
| 7,530,692 | B2 * | 5/2009 | Yamaguchi | A61B 3/1015 351/206 |
| 8,050,482 | B2 * | 11/2011 | Barbu | A61B 6/12 382/128 |
| 8,244,334 | B2 * | 8/2012 | Huang | A61B 3/102 600/476 |
| 8,571,617 | B2 * | 10/2013 | Reichgott | A61B 5/0066 600/310 |
| 8,602,556 | B2 * | 12/2013 | Imamura | A61B 3/1241 351/206 |
| 8,733,933 | B2 * | 5/2014 | Hirose | A61B 3/1025 351/206 |
| 8,770,752 | B2 * | 7/2014 | Hirose | A61B 3/1233 351/206 |
| 9,031,640 | B2 * | 5/2015 | Hachiga | A61B 5/0285 356/342 |
| 9,033,504 | B2 * | 5/2015 | Everett | A61B 3/113 351/210 |
| 2006/0187462 | A1 * | 8/2006 | Srinivasan | A61B 3/102 356/479 |
| 2006/0228011 | A1 * | 10/2006 | Everett | A61B 3/113 382/128 |
| 2008/0007693 | A1 * | 1/2008 | Williams | G06T 5/50 351/221 |
| 2008/0045848 | A1 * | 2/2008 | Lacombe | G01F 1/7086 600/505 |
| 2011/0060232 | A1 | 3/2011 | Lin et al. | |
| 2012/0019780 | A1 * | 1/2012 | Nozato | A61B 3/102 351/221 |
| 2012/0307014 | A1 * | 12/2012 | Wang | A61B 3/102 348/46 |
| 2013/0070201 | A1 * | 3/2013 | Shahidi | A61B 3/1241 351/206 |
| 2013/0321767 | A1 * | 12/2013 | Hirose | A61B 3/1025 351/206 |
| 2014/0073917 | A1 * | 3/2014 | Huang | A61B 5/0066 600/427 |
| 2015/0077706 | A1 * | 3/2015 | Yang | A61B 3/1025 351/206 |

OTHER PUBLICATIONS

Tyson N. Kim, Patrick W. Goodwill, Yeni Chen, Steven M. Conolly, Chris B. Schaffer, Dorian Liepmann, Rong A. Wang. Line-Scanning Particle Image Velocimetry: An Optical Approach for Quantifying a Wide Range of Blood Flow Speeds in Live Animals. PLOS | ONE. Jun. 26, 2012. https://doi.org/10.1371/journal.pone.0038590.*
Scoles, Drew et al., "In Vivo Imaging of Human Cone Photoreceptor Inner Segments," Jul. 2014 Investigative Ophthalmology & Visual Science, vol. 55, No. 7, pp. 4244-4251.
Sulai, Yusufu N. et al., "Visualization of retinal vascular structure and perfusion with a nonconfocal adaptive optics scanning light ophthalmoscope," Mar. 2014, J. Opt. Soc. Am. A, vol. 31, No. 3, pp. 569-579.
Alt, C., et al., "Retinal flow cytometer," 2007 Optics Letter, vol. 32, No. 23 (pp. 3450-3452).
Geng, Y. et al., "Adaptive optics retinal imaging in the living mouse eye," 2012 Biomedical Optics Express, vol. 3, No. 4 (pp. 715-734).
Geng, Y., et al., "Optical properties of the mouse eye," 2011 Biomedical Optics Express, vol. 2, No. 4 (pp. 717-738).
Guevara-Torres, A., et al., "Label free measurement of retinal blood cell flux, velocity, hematocrit and capillary width in the living mouse eye," 2016 Biomedical Optics Express, vol. 7, No. 10 (pp. 4228-4240).
Schallek, J., et al., "Morphology and Topography of Retinal Pericytes in the Living Mouse Retina Using in Vivo Adaptive Optics Imaging and Ex Vivo Characterization," 2013 Investigative Ophthalmology & Visual Science, vol. 54, No. 13 (pp. 8237-8250).
Schallek, Jesse B., et al. "Non-invasive Adaptive Optics Imaging of Retinal Pericytes and Capillary Blood Velocity in Mice," 2012 Journal of Vision, vol. 12 (2 pgs).
Tuchin, V. et al., "In Vivo Flow Cytometry: A Horizon of Opportunities", 2011 Cytometry, vol. 79A (pp. 737-745).

* cited by examiner

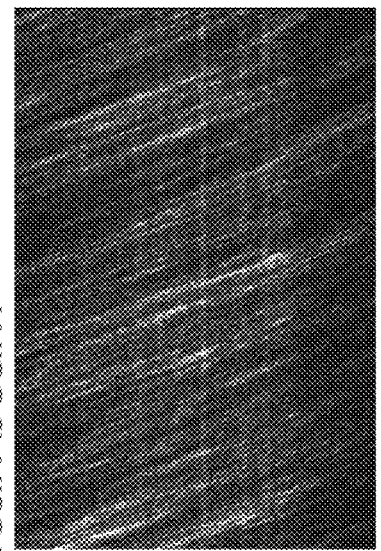
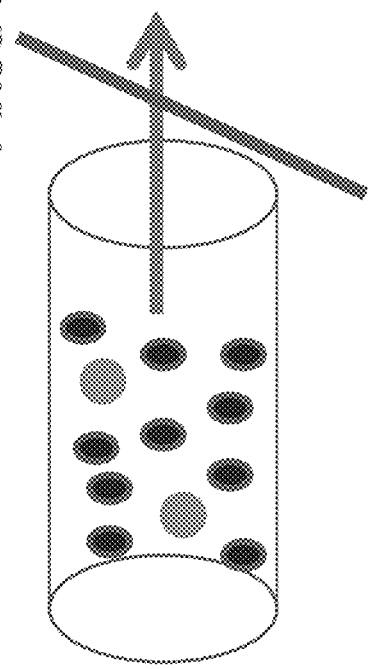
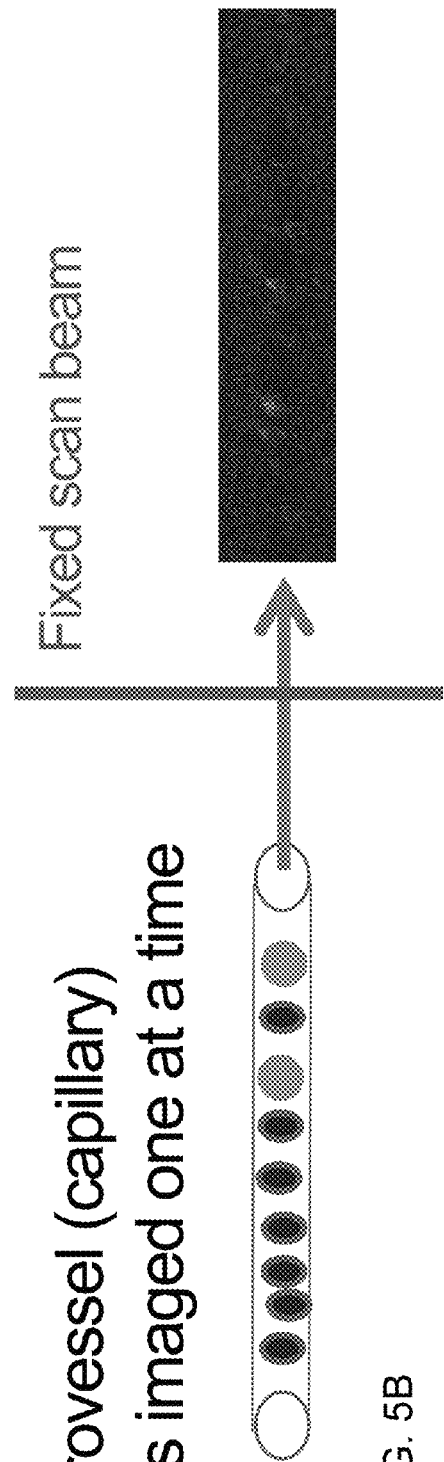
FIG. 5A
Large vessel allows multiple cells imaged at the same time
FIG. 5B
Microvessel (capillary) Cells imaged one at a time

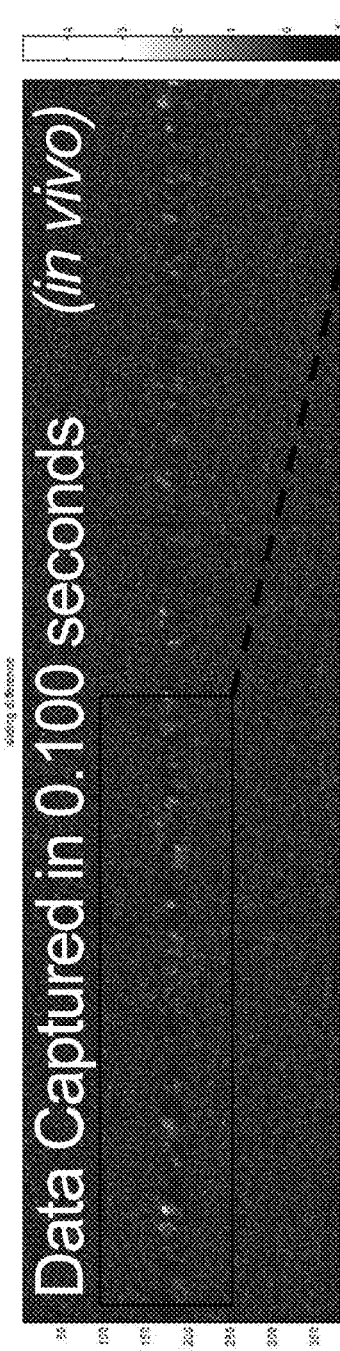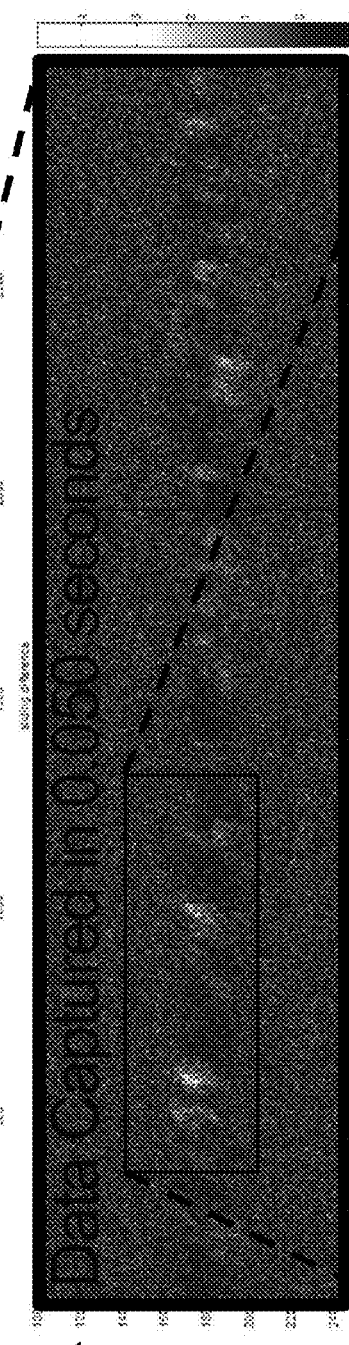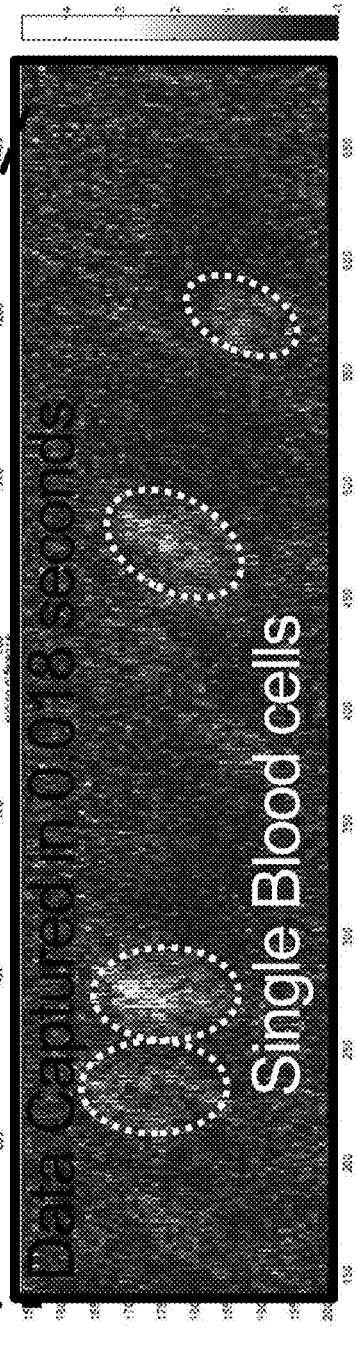
FIG. 8A
FIG. 8B
FIG. 8C

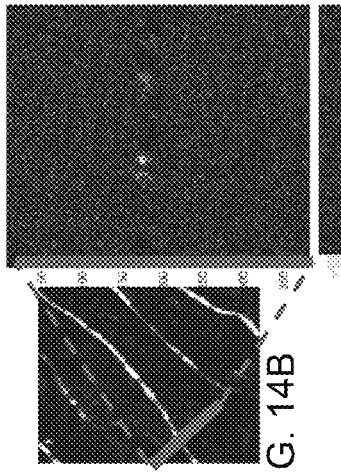
FIG. 14B
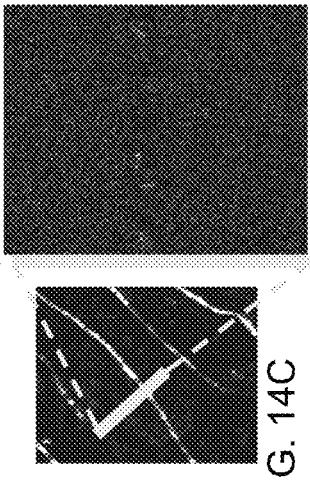
FIG. 14C
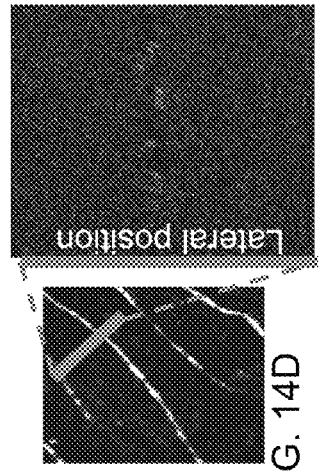
FIG. 14D
FIG. 14A

SYSTEM AND METHOD FOR OBSERVING AN OBJECT IN A BLOOD VESSEL

CROSS-REFERENCE TO RELATED APPLICATIONS

This application claims the benefit under 35 U.S.C §119 (e) to U.S. Provisional Application No. 61/933,102, SYSTEM AND METHOD FOR OBSERVING AN OBJECT IN A BLOOD VESSEL, filed Jan. 29, 2014, which application is incorporated herein by reference in their entirety.

STATEMENT REGARDING FEDERALLY FUNDED RESEARCH OR DEVELOPMENT

This invention was made with government support under EY014375 and EY001319 awarded by the National Institutes of Health. The government has certain rights in the invention.

FIELD OF THE APPLICATION

The application relates to In Vivo imaging of blood vessels and particularly to In Vivo remote sensing of moving objects in blood vessels.

BACKGROUND

In vivo two dimensional (2D) imaging of blood vessels and blood cells has been done using imaging techniques, such as laser scanning techniques. For example, the adaptive optics scanning light ophthalmoscope (AOSLO) has been used to create 2D images of the retina of the eye.

SUMMARY

According to one aspect, a method for creating a virtual 2D image of an object moving in a blood vessel includes the steps of: providing an imaging apparatus capable of acquiring 1D images, the imaging apparatus communicatively coupled to a computer; acquiring multiple 1D images of a substantially fixed footprint on a surface of an organ over a period of time; combining by computer the multiple 1D images to form a virtual 2D image showing the object moving in the blood vessel; and performing at least a selected one of: displaying the virtual 2D image and saving the virtual 2D image to a non-volatile memory.

In one embodiment, the step of acquiring multiple 1D images includes acquiring multiple 1D images of a substantially fixed footprint on a surface of an organ as viewed through one or more intermediate transparent or translucent layers of the organ or of another organ.

In another embodiment, the step of providing an imaging apparatus includes the step of providing a 1D imager communicatively coupled to a computer, the 1D imager having an imaging width which is much smaller than an image length.

In yet another embodiment, the step of acquiring multiple 1D images includes the step of acquiring by the computer the 1D images and storing the 1D images in a non-volatile memory.

In yet another embodiment, the step of acquiring multiple 1D images includes the step of positioning the 1D imager to image a substantially fixed 1D footprint at the surface having one or more blood vessels, the 1D footprint transecting the one or more blood vessels, the 1D imager stationary except for an optional adaptive movement of the 1D imager to track undesired movement of the surface.

In yet another embodiment, the step of combining by computer the multiple 1D images includes concatenating by the computer a plurality of substantially successive 1D images to create a virtual 2D spatio-temporal image which includes information of a movement of the object traveling through a blood vessel of the one or more blood vessels, and storing the virtual 2D spatio-temporal image in a non-volatile memory.

In yet another embodiment, the step of calculating by the computer a velocity of the object based on at least a subset of the multiple 1D images.

In yet another embodiment, the step of calculating by the computer a shape of the object based on at least a subset of the multiple 1D images.

In yet another embodiment, the method further includes the step of calculating by the computer a type of the object based on at least a subset of the multiple 1D images.

In yet another embodiment, the object includes a blood cell.

In yet another embodiment, the object includes a diagnostic object.

In yet another embodiment, the method further includes one or more additional imagers and wherein the step of acquiring multiple 1D images includes acquiring multiple 1D images from multiple imagers over a period of time of two or more substantially fixed footprint on the surface of the organ and the step of combining by computer includes combining by computer the multiple 1D images from the two or more substantially fixed footprints to form two or more virtual 2D image showing the object moving in the blood vessel.

In yet another embodiment, the method further includes after the step of combining by computer the multiple 1D images, performing a spatio-temporal cross correlation between at least two of the two or more virtual 2D images.

In yet another embodiment, the method is repeated at two or more different substantially fixed 1D footprints so as not to exceed a pre-determined exposure limit According another aspect, a system for observing a movement of an object in a blood vessel includes a 1D imager configured to generate a plurality of 1D images over a period of time of a substantially fixed location on a surface having one or more blood vessels. A support structure is mechanically coupled to the 1D imager and configured to adjustably position the 1D imager in a substantially fixed direction during a 1D successive line imaging of the substantially fixed location on the surface, except for optional adaptive movement of the 1D imager to track the movement of the substantially fixed location. A computer is communicatively coupled to the 1D imager and configured to receive successive 1D images of the plurality of 1D images in time from the 1D imager. The computer is communicatively coupled to a non-volatile memory configured to store the successive 1D images. The computer is configured to generate a concatenation of the 1D images to create a virtual 2D spatio-temporal image which includes information of a movement of the object traveling through the blood vessel of the one or more blood vessels.

In one embodiment, the 1D imager includes an adaptive optics scanning light ophthalmoscope (AOSLO) or a scanning light ophthalmoscope (SLO).

In another embodiment, the 1D imager includes an optical coherence tomography (OCT) imager.

In yet another embodiment, the 1D imager includes a 1D slit camera.

In yet another embodiment, the 1D imager includes a M×N pixel imaging device.

In yet another embodiment, the system is configured such that light returned from the substantially fixed location on the surface is directed to a detector selected from the group consisting of fluorescence, long wavelength, mid wavelength, short wavelength, forward scatter, back scatter, and birefringence.

In yet another embodiment, the 1D imager includes at least one beam splitter configured to direct light returned from the substantially fixed location on the surface simultaneously to two or more detectors.

In yet another embodiment, the system is further configured to move the substantially fixed location to another substantially fixed location after a pre-determined exposure threshold has been reached.

According another aspect, a method for creating a virtual 1D image of an object moving in a blood vessel includes the steps of: providing an imaging apparatus capable of acquiring single point images, the imaging apparatus communicatively coupled to a computer; acquiring multiple single point images over a period of time of a substantially fixed footprint on a surface of an organ; combining by computer the multiple single point images to form a virtual 1D image showing the object moving in the blood vessel; and performing at least a selected one of: displaying the virtual 1D image and saving the virtual 1D image to a non-volatile memory.

The foregoing and other objects, aspects, features, and advantages of the invention will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 5A shows an exemplary illustration of a large blood vessel which allows multiple cells to pass at the same time next to an exemplary corresponding 1D successive line image;

FIG. 5B shows an illustration of an exemplary capillary showing a single file passage of individual cells next to an exemplary corresponding 1D successive line image;

FIG. 8A shows the exemplary scan of FIG. 7, where the boxed area shows an area to be magnified;

FIG. 8B shows a magnified view of FIG. 8A;

FIG. 8C shows a magnified view of FIG. 8B;

FIG. 14A shows a 2D image overlaid by three exemplary 1D fixed footprint imaging sites;

FIG. 14B shows the first of the 1D fixed footprint imaging sites of FIG. 14A and a corresponding 1D successive line scan image;

FIG. 14C shows the second of the 1D fixed footprint imaging sites of FIG. 14A and a corresponding 1D successive line scan image;

FIG. 14D shows the third of the 1D fixed footprint imaging sites of FIG. 14A and a corresponding 1D successive line scan image;

DETAILED DESCRIPTION

Figure 1:
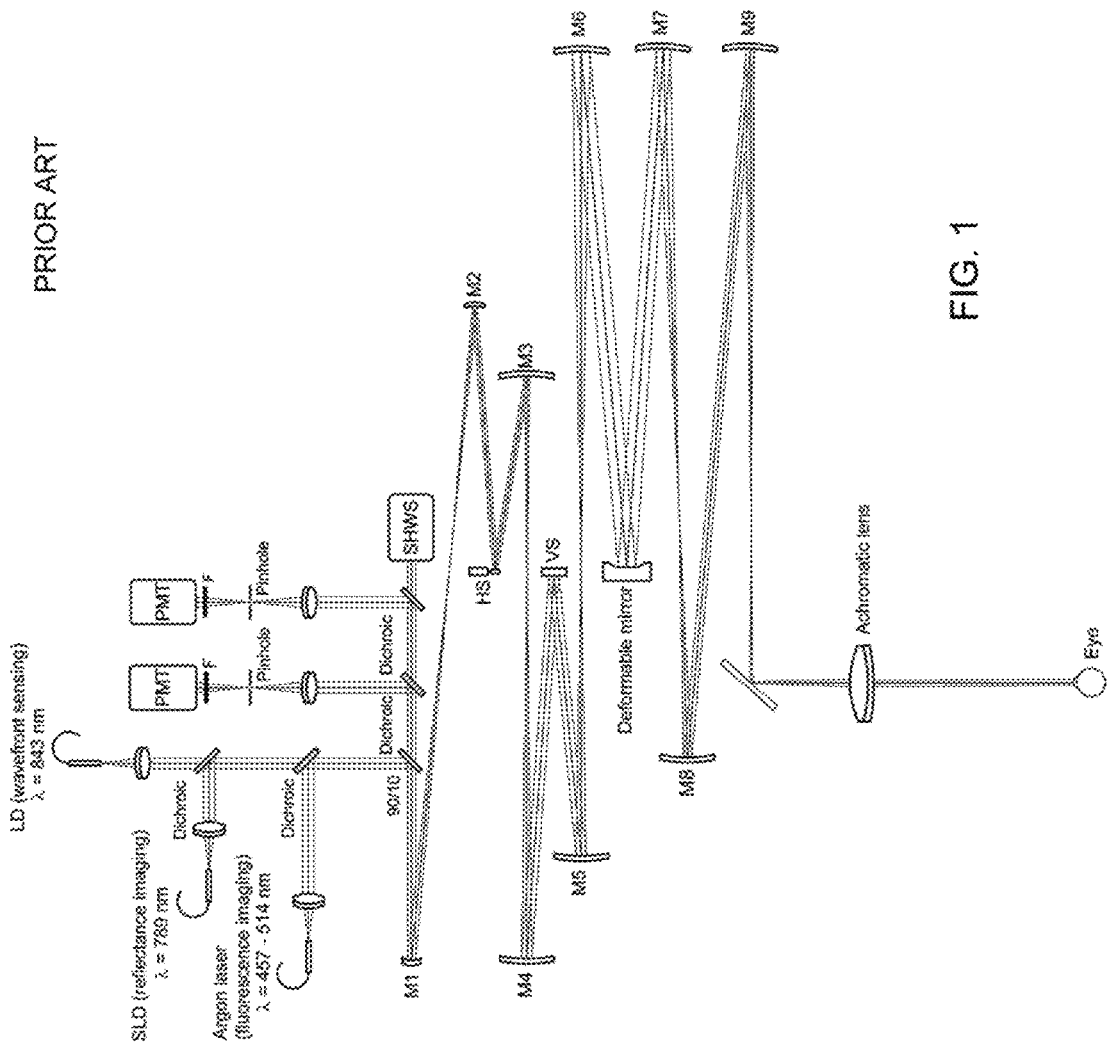
FIG. 1 shows a schematic diagram of a prior art 2D adaptive optics scanning light ophthalmoscope (AOSLO)

In the description, other than the bolded paragraph numbers, non-bolded square brackets ("[ ]") refer to the citations listed hereinbelow.

Definitions:

Successive line scans:Successive line scans (e.g. acquiring multiple one dimensional (1D) images by line scanning or line imaging) are defined as a plurality of 1D line scans or 1D images acquired over a period of time, wherein successive lines scans or line images are of the same substantially fixed line (e.g. a substantially fixed footprint) of a surface being imaged, each 1D scan or 1D image set apart from the previous 1D scan or 1D by an advance of time between the successive 1D scans or 1D images.

The time for a single scan can include the time to form a 1D line image (e.g. an exposure or integration time) or the time to scan each of the 1D line images (e.g. the time to scan the LASER of a scanning LASER system a desired arc length to image a desired length of a 1D scan over surface), and any dwell time between scans which can include writing the previous 1D scan to non-volatile memory, and, for example, to return a LASER or a scanning LASER system to a start point.

While LASER scanning techniques generally use a LASER, it is also understood that any suitable relatively high brightness about point source of light (i.e. relatively narrow beamwidth) can be used. For example, many types of high brightness light emitting diodes (LEDs) can be used for such an application. Also, as described hereinbelow in more detail, in place of exemplary point source light techniques, any suitable imager can be used using any suitable lighting.

Successive line images including a succession of 1D scans, or 1D images, can be made using any suitable 1D line scanning or line imaging system. A 1D line image can include any 1D image of 1 pixel to $N_w$ pixels wide by $N_L$ pixels long where $N_L$ is greater than $N_w$ by a ratio of at least about 10. The definition of Successive 1D line scans includes successive line images made by any suitable 1D imaging system includes, for example, a 1D CMOS imager. It is unimportant to the inventive method if pixels of a 1D line image are read or measured in scanning succession (e.g. SLO or AO-SLO type instruments) or if all of the pixels in a 1D line image are simultaneously exposed to light from the 1D line on the surface and read at the same time or in any other suitable read order. Any suitable imaging apparatus can be used. The 1D imaging width is typically much smaller than an image length along a length axis.

Typically, a predetermined number successive line images are acquired by a computer. Any suitable type of computer can be used ranging from an embedded computer or embedded microprocessor or microcontroller internal to the 1D imaging apparatus to any suitable computer external to the imaging apparatus. Also, as described in more detail hereinbelow, a predetermined number successive line images can be acquired at multiple substantially fixed positions on a surface, such as for reasons to limit exposure to optical power at any one physical location.

A virtual two dimensional (2D) or "2D like" 1D-successive time image (e.g. a virtual 2D spatio-temporal image) can be derived from a concatenation of successive 1D line scans taken of the substantially same 1D line location on a surface at different times over a time period. Thus, 1D-successive time images distinguish over 2D prior art imaging techniques in that successive lines of prior art 2D images, to the extent that an analogy can be made, are made by, or show a physical advance along a surface being imaged in a direction normal or perpendicular to the 1D axis. By contrast, 1D line scans show substantially the same 1D line on the surface being imaged many times at some time interval over a period of time of the 1D-successive time image which results in the "2D like image" having a physical 1D distance along the surface typically along a 1D-successive time image vertical axis and a time period typically along a 1D-successive time image horizontal axis.

Successive 1D line scans or images can be thus be transformed into a virtual two dimensional (2D) or "2D like" 1D-successive time image (e.g. a virtual 2D spatio-temporal image).

1D footprint:1D footprint refers to a length and more narrow width compared with the length (e.g. the width is typically less than at least about ten times the width) on a surface to be imaged.

A surface to be 1D imaged is typically separated from the 1D imager apparatus by one or more intermediate transparent, semi-transparent, or translucent surfaces. The substantially fixed 1D footprint can be, and is often, on a surface of an organ viewed through one or more transparent or translucent intermediate layers of the organ or another organ. For example, blood cells in blood vessels in the retina of the eye can be imaged through the cornea, the aqueous humor of the anterior chamber, the pupil of the iris, the lens, the vitreous humor of the vitreous cavity of the eye, and the wall of the blood vessel. 1D imagers typically include any suitable type of mechanical support structure so that the 1D imager can be adjustably pointed (typically by computer control) to one or more 1D footprints on the surface to be imaged.

Transecting a blood vessel: Transecting a blood vessel means that the blood vessel has a non-zero angle with the 1D foot print (e.g. not exactly parallel to the 1D foot print). In the methods described herein, the 1D footprint typically transects at least one blood vessel.

Object moving in a blood vessel: Typically blood cells moving through blood vessels (including, for example, blood capillaries) are the objects of study. However, any natural or foreign matter objects (e.g. a diagnostic object) moving through a blood vessel which can be distinguished from the walls of the blood vessel can be studied using the new 1D successive imaging techniques described herein.

Also, any media moving through a blood vessel can be observed. Such media includes, for example, blood plasma in which blood cells are suspended, artificial agents, tracers, and/or dyes. Exemplary tracers and dyes include indocyanine green, sodium fluorescein, and acridine orange.

As described hereinabove, the adaptive optics scanning light ophthalmoscope (AOSLO) is an example of a 2D imaging tool currently known in the art. For example, the University of Rochester reported use of custom fluorescence AOSLO for imaging the mouse eye as described by Geng, et. al. in Adaptive optics retinal imaging in the living mouse eye, Biomedical Optics Express, April 2012/Vol. 3, No. 4, pages 715, 734. A schematic layout of the prior art Geng system is shown in FIG. 1.

AOSLO techniques of the prior art generally include a relatively fast laser based line scanner coupled with movement of the line scan typically in a transverse direction (about normal to the one dimensional (1D) line scan) so that successive 1D scans advance in the transverse direction across the surface being imaged, to generate a two dimensional (2D) image of an area. The 1D line scans are typically relatively narrow. In the case of analog sensing, such as for example by laser light reflected back to and detected by a photo-multiplier tube (PMT), the line scan data is generally digitized typically resulting in a one pixel wide digital representation of the 1D line. Also, as is known in biomedical applications, the surface area being scanned can be a subsurface structure, such as for example structures of the human or animal eye as scanned through one or more intermediate transparent, semitransparent, or translucent structures.

Spatio-temporal imaging: A new type of system and method for in vivo blood vessel measurement is now described. AOSLO technology has advanced to yield high resolution 2D images of 2D fixed surfaces and 2D moving surfaces.

It was further realized that movement across the surface can be imaged by removing the transverse scanning mechanism (typically a moving minor). That is, it was realized that movement across the surface and properties of objects moving on or below a surface can be studied by use of a stationary line scan at a substantially fixed line on a 2D surface under study. It was further realized that any motion or movement across the scan line at any angle other than the direction of the 1D scan line itself, causes the object moving across the 1D scan line to "self-scan itself" as the object passes across the line of a 1D scan or 1D image. Moreover, in addition to a resultant spatio-temporal "2D like" image of one or more self-scanned objects (by combining successive 1D line scans), by accounting for the 1D scan time the self-scanned image can also reveal the velocity of the object.

The 1D successive line imaging technique, as is described in more detail hereinbelow, is believed to be applicable to a number of biomedical imaging systems as well as to the specific application for which it was initially developed, imaging objects moving through a blood vessel. The 1D imaging technique can be accomplished using a prior art AOSLO with the vertical scanner (the transverse scanner) turned off, or removed. The 1D imaging technique is referred to herein as a successive line scan, 1D successive line scan, or line imaging technique.

Figure 2:
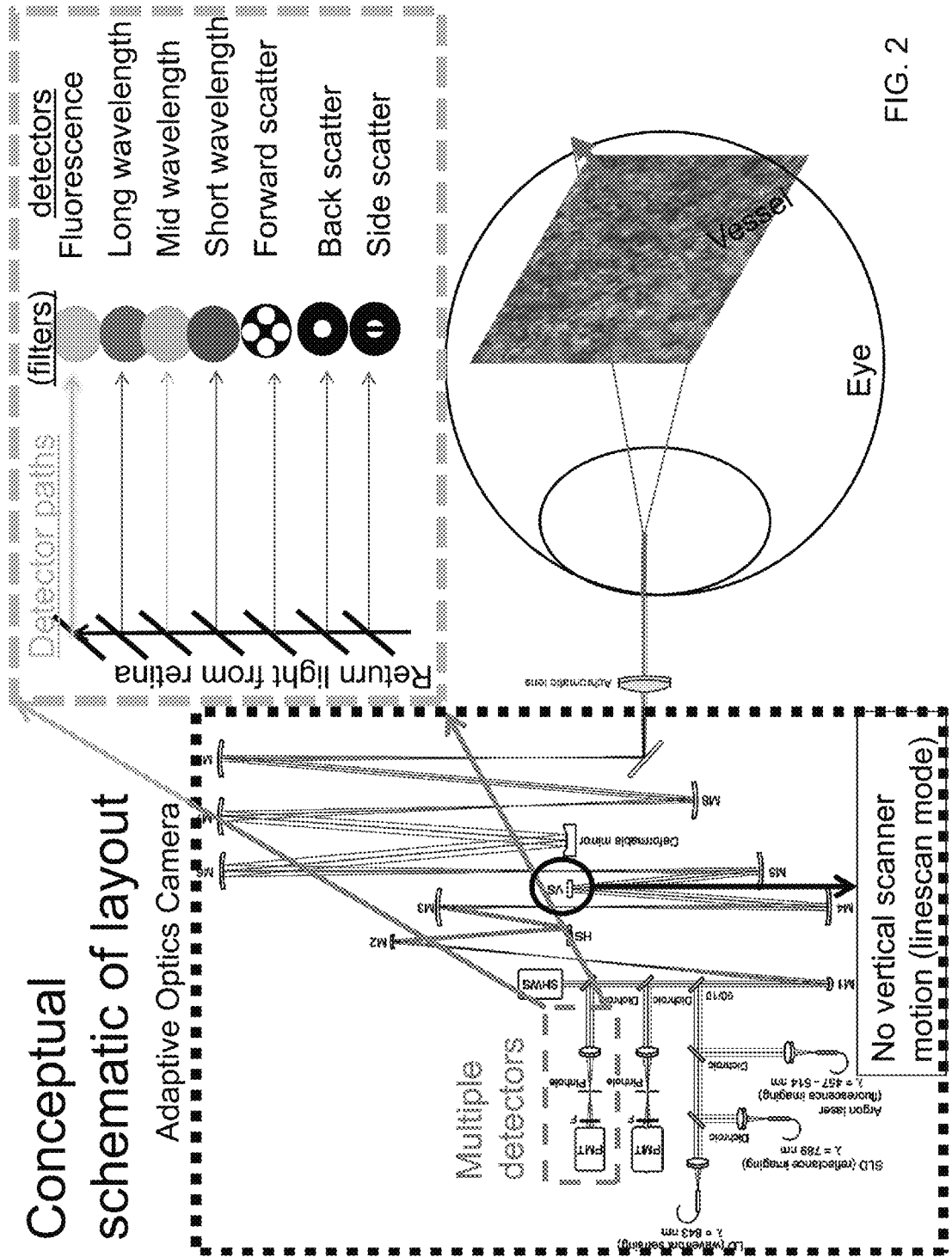
FIG. 2 shows a conceptual schematic diagram of an exemplary AOSLO imager suitable for performing the new one dimensional (1D) successive stationary line scan techniques.

FIG. 2 shows a conceptual schematic of an exemplary 1D AOSLO imager based on the AOSLO system of FIG. 1. As illustrated by FIG. 2, in some embodiments, the light returning from the illuminating laser sourced 1D scan line can be split into a plurality of paths and simultaneously viewed through a variety of filters, such as, for example, fluorescence, long wavelength, mid wavelength, short wavelength, and/or a variety of return paths and mechanisms, such as, for example, forward scatter, back scatter, or side scatter.

Experimental studies have demonstrated that high resolution 1D imaging can provide a reliable way for detecting cell movement with a sub-micron lateral resolution. In one embodiment, without traditional vertical scanner motion (e.g. a 2D AOSLO converted to the new 1D successive line scan mode), rapid acquisition in the time domain (e.g. greater than about 30 kHz) allows for a rapid data collection in the temporal regime. For example, a single 1D line scanned across a vessel allows blood cells traveling through the blood vessel to "self-scan" themselves as they pass across the substantially fixed position 1D scan line. For example in a scanning LASER system, a single detector is sufficient for a blood cell to self-scan itself. In other embodiments, using multiple detectors combined with splitting the returned light into multiple channels enables simultaneous detection of multi-parameter data. For example, there can be light paths and sensors to receive and detect forward scattered light, back scattered light, and side scatter light (e.g. by using multiple pinhole detection including obscured pinhole paradigms), light from fluorescence and/or light absorption profiles using bandpass filters. Moreover, correlation and/or decorrelation of these simultaneously captured channels can be used during data analysis for cell classification based on the optical properties of passing cells.

Figure 3:
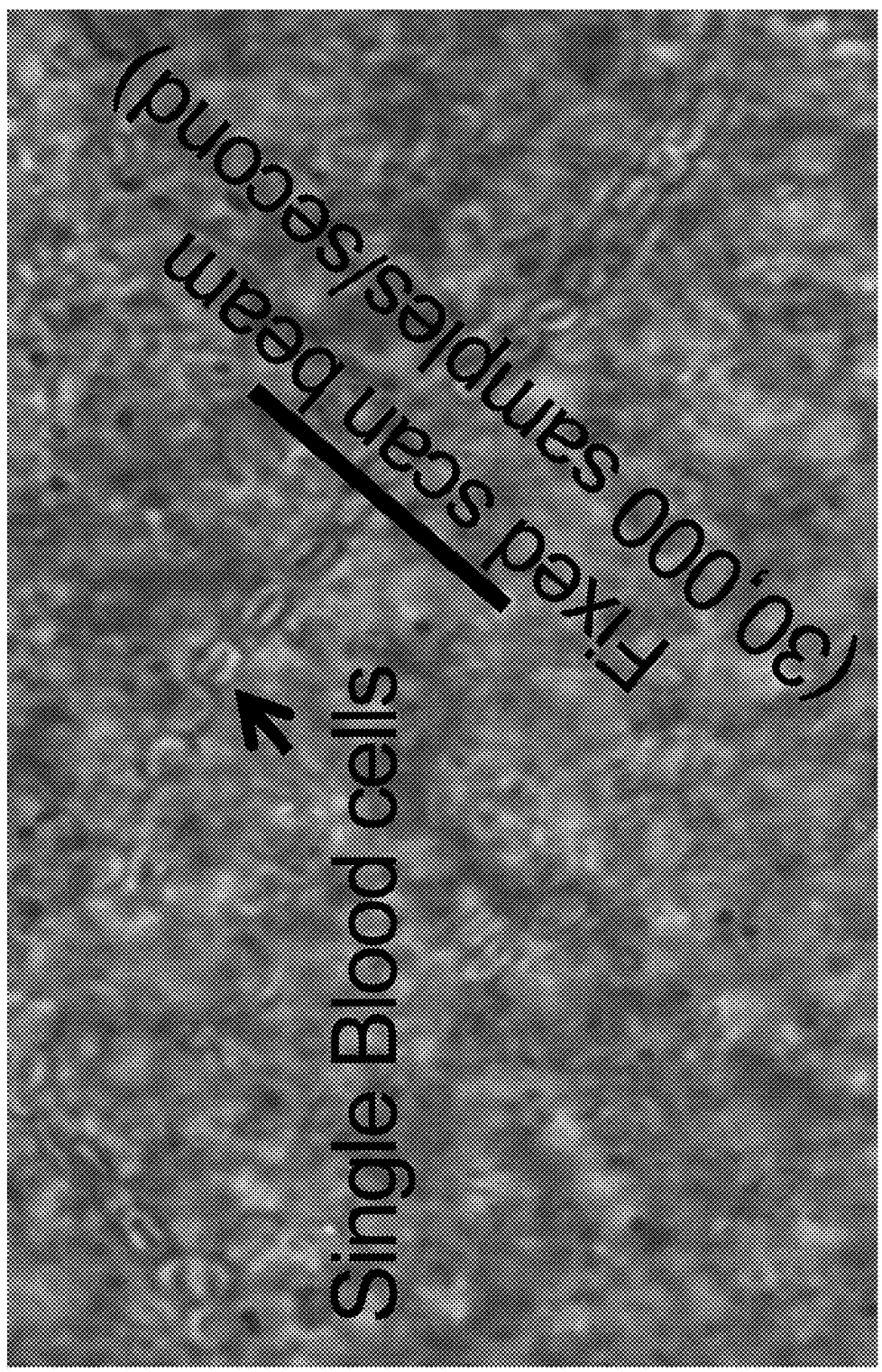
FIG. 3 shows a conventional 2D image of the retina of an eye with a superimposed fixed scan line representing the new 1D method.

FIG. 3 shows a conventional 2D image of a retina. The superimposed line drawn over the image shows an exemplary 1D substantially fixed position 1D scan line. The line has been oriented about perpendicular to a small blood vessel. The arrow points to a blood cell. The conventional image of FIG. 3 is shown to illustrate the 1D approach. In this exemplary embodiment, a LASER beam is scanned across a retinal vessel (the line representing a 1D line scan position according to the technique described herein). As blood cells move across the beam, the shape and optical properties of each cell can be recorded. Facilitating this analysis is the known property that blood cells in microvessels pass one-by-one.

Figure 4A:
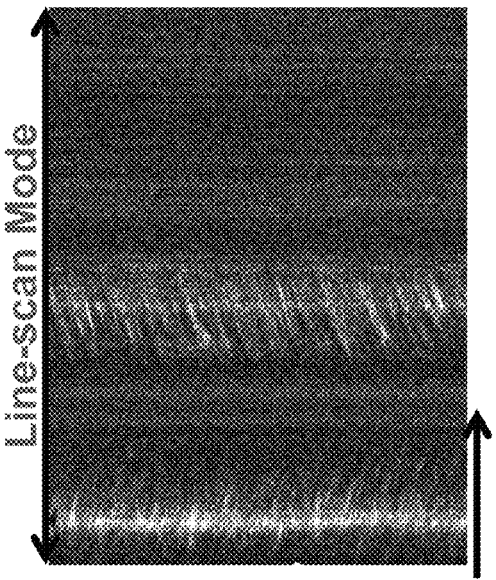
FIG. 4A shows a conventional 2D AOSLO image.
Figure 4B:
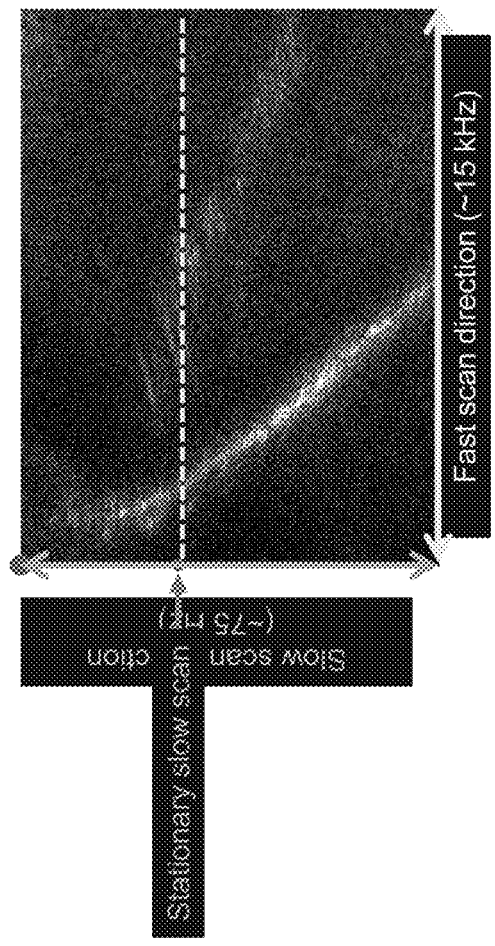
FIG. 4B shows a sequence of successive 2D Cartesian images.
Figure 4C:
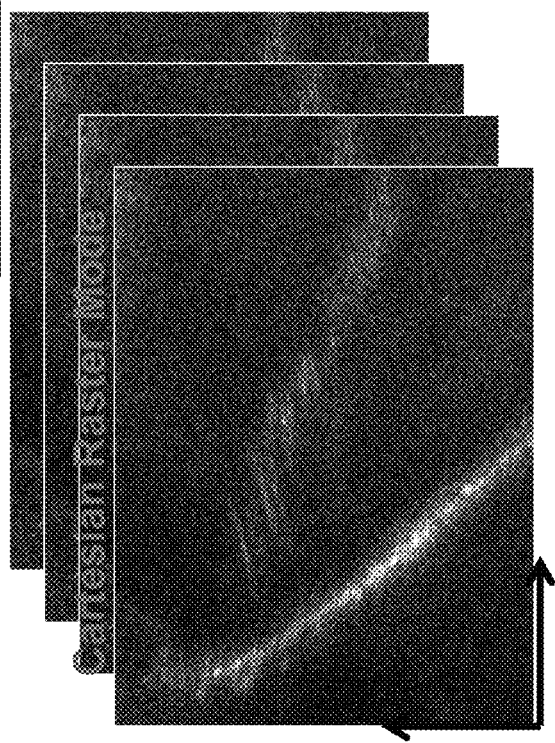
FIG. 4C shows an image made according to the new method of successive line scans.

FIG. 4A shows a conventional 2D AOSLO image derived from an exemplary fast scan (~15 kHz) combined with a slow scan of about 75 Hz using an AOSLO system such as is shown in FIG. 1. FIG. 4B shows a sequence of successive 2D Cartesian images (it is common practice in conventional AOSLO to average or otherwise combine successive 2D image scans, for example, to reduce noise). By contrast, FIG. 4C show a line scan made according to the new 1D technique described herein. The line scan is directed to a substantially fixed location on the surface to be scanned in 1D. The 1D line is not moved or scanned as is done in prior art 2D AOSLO scanning The "2D like" view of FIG. 4C shows a succession of 1D line scans computer drawn next to each other to form a "virtual 2D image". Note that if nothing moves across the 1D line scan, the image would be monotonic. However, in FIG. 4C there are a number of objects (e.g. blood cells) which have moved across the 1D line, thus self-scanning themselves.

FIG. 5A shows an exemplary illustration of a larger blood vessel which allows multiple cells (e.g. blood cells) to pass at the same time which results in the pattern of the corresponding image, somewhat similar to the exemplary image of FIG. 4C. On the other hand, microvessels (e.g. capillaries) allow only one cell to pass at one time. FIG. 5B shows an illustration of an exemplary capillary and a resultant image using the 1D fixed scan technique can yield a different type of image, showing passage of the individual cells.

Figure 6:
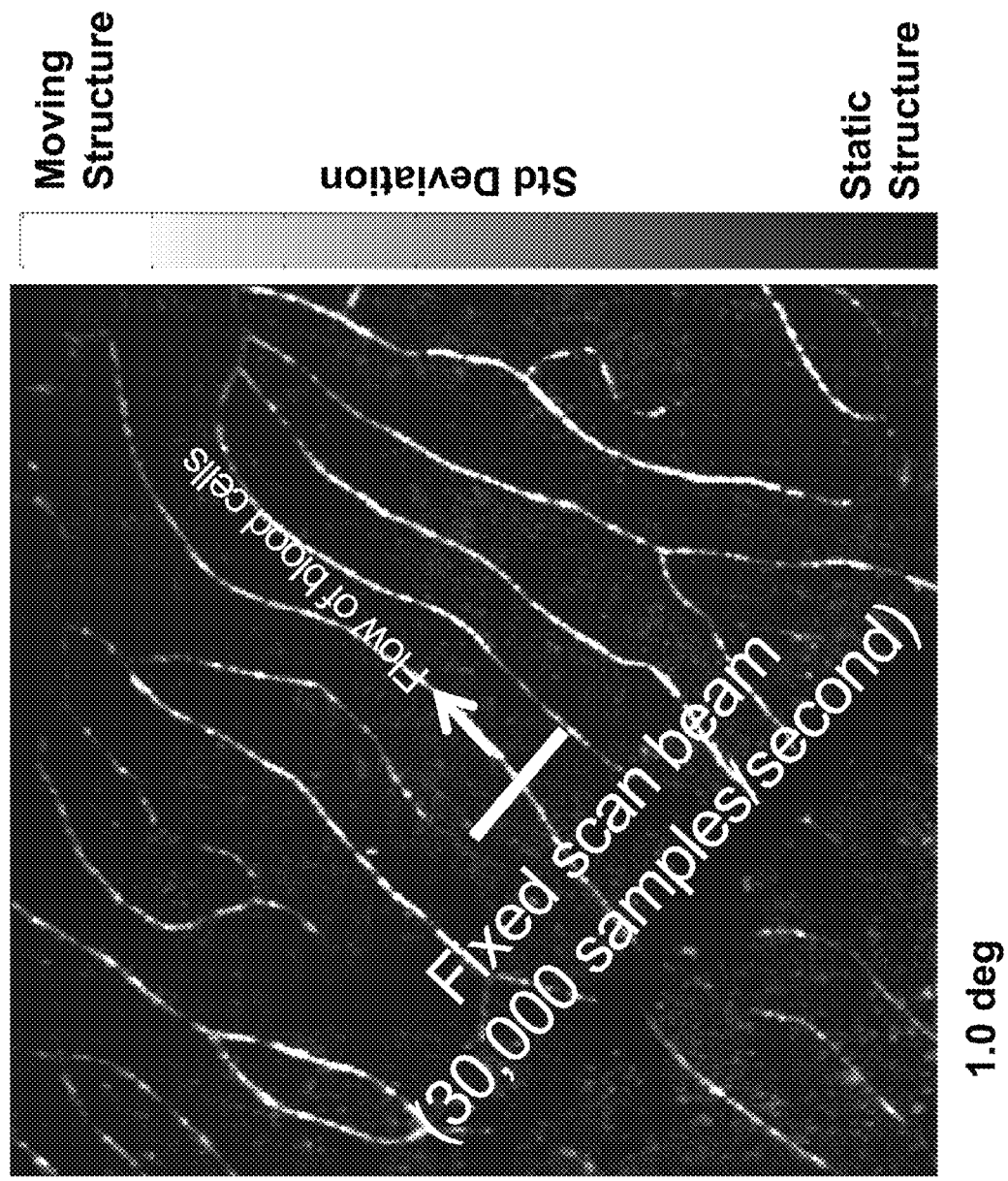
FIG. 6 shows an exemplary 2D capillary map image with a superimposed fixed 1D scan beam line.
Figure 7:
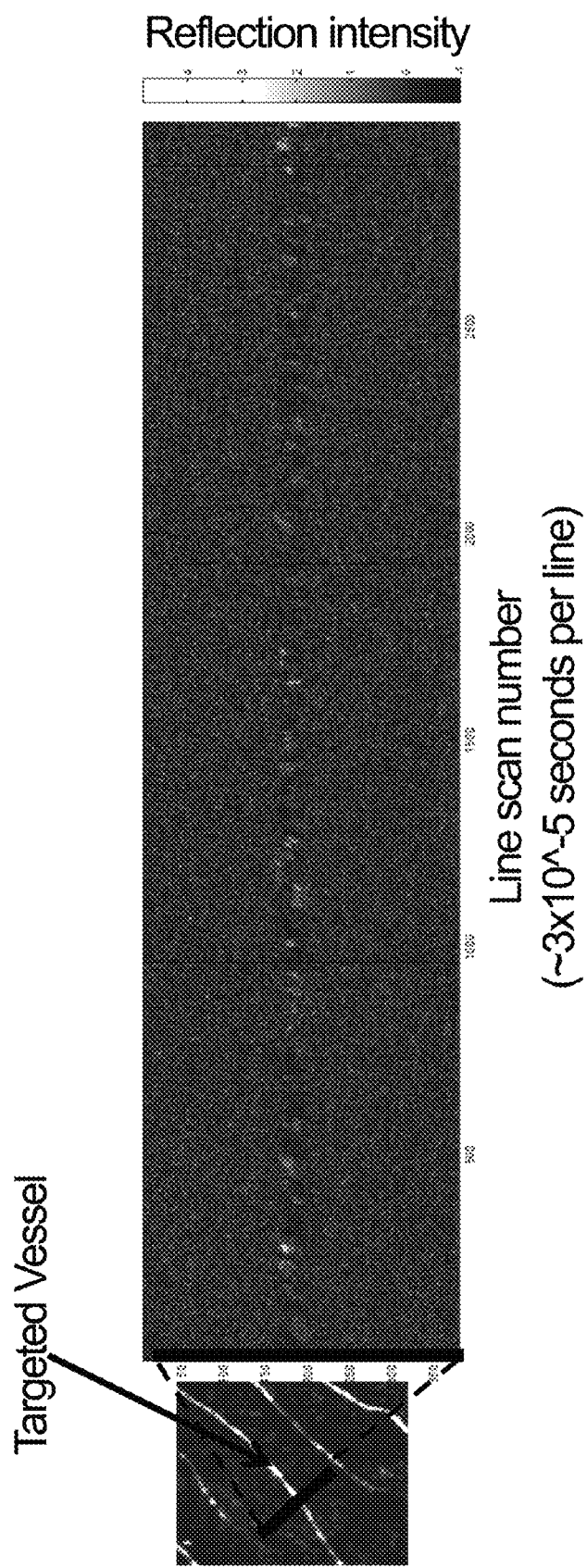
FIG. 7 shows a small area view of a portion of FIG. 6 to the left, and to the right a successive line scan image according to the new method.

FIG. 6 shows an exemplary capillary map image captured by a 2D Cartesian raster mode scan. Similar to FIG. 3, the line drawn about perpendicular to the flow of blood cells in one of the capillaries shows where a 1D substantially fixed scan according to the 1D techniques described herein is made. FIG. 7 shows a small area view of a portion of FIG. 6 to the left, and to the right a series of about 3000 successive line scans stacked next to each other horizontally (the x-axis shows line scan numbers) and the y-axis is a distance scanned on the line at and along the surface across the line being imaged, along the line scan. The line scans were made at a rate of about 30 μs/line. The image of FIG. 7 represents a total scan time of about 200 ms or about two tenths of a second.

Imaging through intermediate structures: Note that the surface being imaged using techniques described herein, especially typical in ophthalmic imaging, is typically below outer transparent or semi-transparent surfaces (e.g. as in imaging structures of the eye). Blood cells (or, any other objects) can be seen to be self-scanned as they pass across the substantially fixed 1D line scan. Individual blood cells can be clearly distinguished from one another.

FIG. 8A shows the exemplary scan of FIG. 7. The boxed area in FIG. 8A indicates the area that was magnified and which is shown below FIG. 8A in FIG. 8B. Note that "zooming in" in the vertical direction of a 1D successive line scanned image corresponds to literally magnifying in distance, however magnification in the horizontal direction corresponds to observing a shorter period of time (i.e. fewer scans). FIG. 8B, shows a magnified view of FIG. 8A of about 0.2 seconds (about 3,000 scans) over about 0.1 seconds with about 1500 line scans. FIG. 8B, shows a magnified view of the about 350 μm vertical imaging scale of FIG. 8A magnified to about a 150 μm vertical imaging scale. Similarly, the box in FIG. 8B indicates a second zoom of the image of FIG. 8B shown below FIG. 8B in FIG. 8C. FIG. 8C shows a magnified view compared to FIG. 8B with about 1,500 scans over about 0.018 seconds (18 ms) with about 700 line scans. FIG. 8C, shows a magnified view of the 150 μm vertical imaging scale of FIG. 8B magnified to about a 50 μm vertical imaging scale in FIG. 8C. While individual blood cells can be seen in FIG. 8A, FIG. 8B, and FIG. 8C, by the magnification in distance (vertical axis) and time (horizontal axis) of FIG. 8C, four individual blood cells are clearly in view.

Blood cell identification and size: It is contemplated that with the detailed 1D successive line scanning technique as described herein and as illustrated, for example, by FIG. 8A, FIG. 8B, and FIG. 8C, that automatic identification of blood cells can be done by computer, such as, for example, by use of a computer program that searches for objects with width consistent with that of blood cells or certain types of blood cells.

Figure 9A:
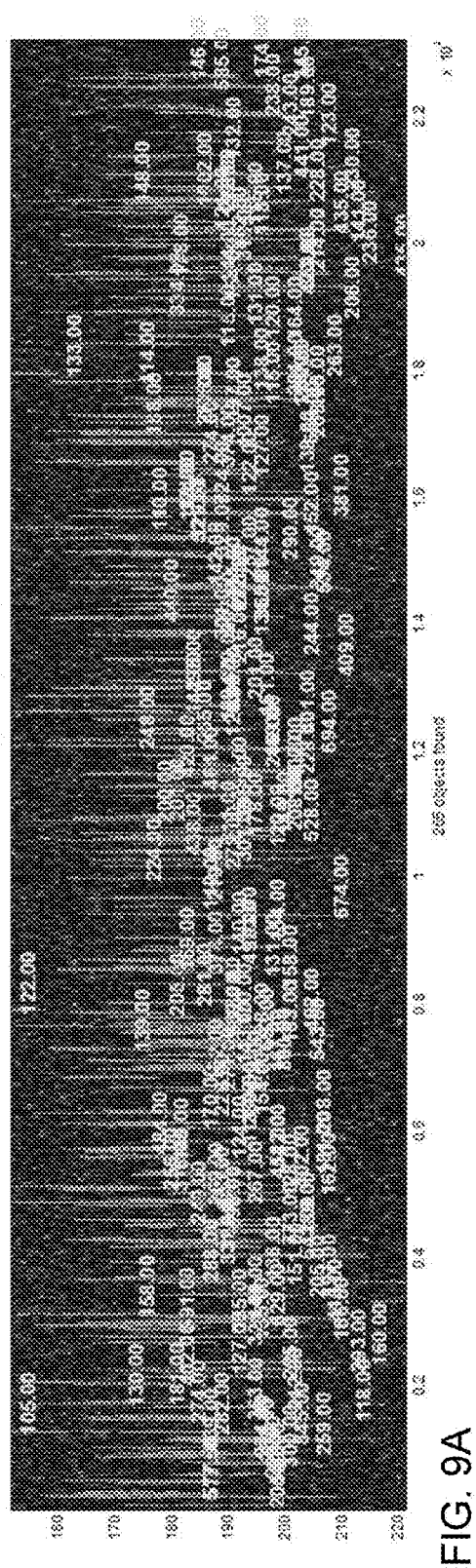
FIG. 9A shows 1D successive line image of about 23,000 line scans.
Figure 9B:
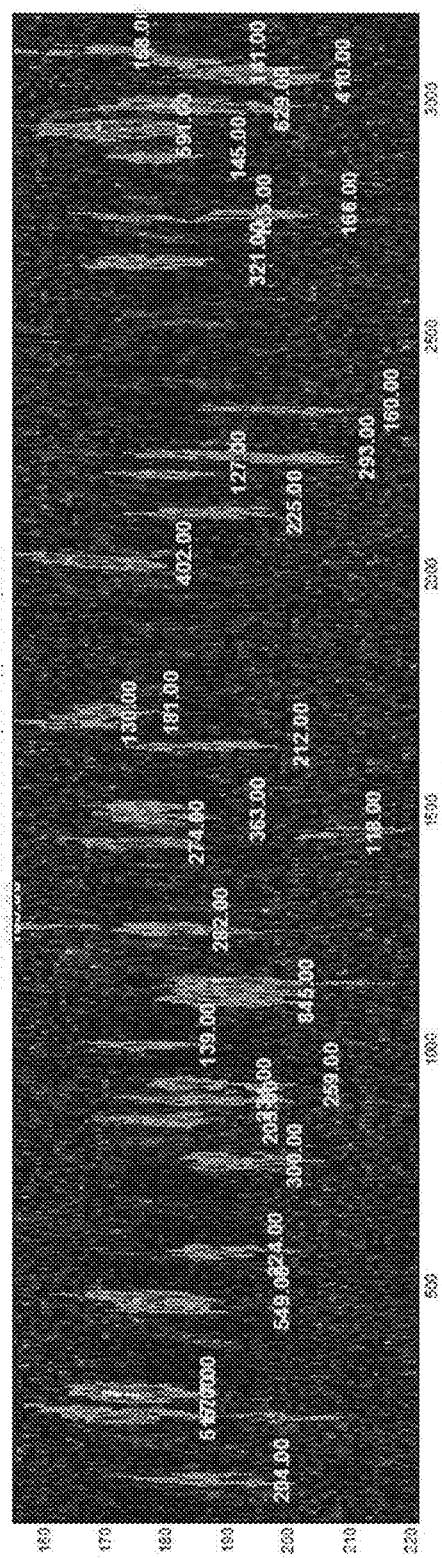
FIG. 9B shows a magnified view of FIG. 9A of about 3,200 line scans.
Figure 9C:
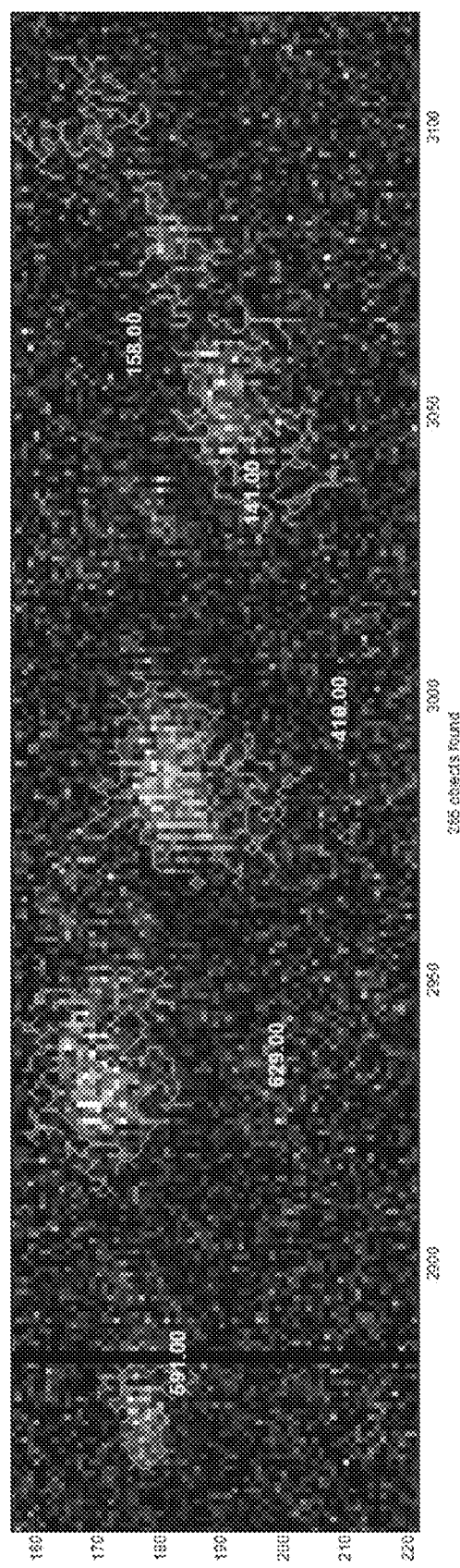
FIG. 9C shows a magnified view of FIG. 9B of about 350 line scans.

FIG. 9A, FIG. 9B, and FIG. 9C show various views of another exemplary line scan made by the 1D successive line scanning technique as described herein. FIG. 9A shows 1D successive line image about 100 μm wide by 2200 line scans at about 30 k samples/second made over about 0.73 seconds. The exemplary computer cell identification process can be seen to have identified and labeled automatically about 265 blood cells on the 1D successive line scanned image. FIG. 9B shows a first magnified view in time (magnified over the horizontal axis) yielding a more detailed view of a number of computer process auto-identified cells of about 3200 lines over about 0.1 seconds. FIG. 9C shows yet a more detailed view of about 275 line scans over about 0.01 seconds (10 ms). Note that by the magnification of FIG. 9C, individual pixels of each one pixel wide line can be seen. Also, the computer process can optionally automatically identify a center or "center of mass" of each cell by a computer calculation of the weighted centroid of each identified object. The numbers next to each cell indicate the area of the cell in units of pixels$^2$.

Each 1D line scan has some finite width in the transverse direction (normal to the longer 1D line) associated with each "1 pixel wide" line. For example, the exemplary images of FIG. 9A to FIG. 9C have an optical resolution of about 700 nanometers (lateral resolution). Sampling with more than 1 pixel per 700 nanometers can also be used for oversampling the data. Oversampling can provide the benefit of spatially averaging the pixels without losing optical resolution.

Blood cell identification and speed: It is contemplated that with the detailed 1D successive line scanning technique as described herein that automatic calculation of blood cell velocity through blood vessels can optionally be performed by a computer. Cell speed (as well as the speed of any other objects traveling through blood vessels) can be measured by computing "elongation ratio" of the objects, typically moving blood cells. Blood cells, especially red blood cells, are generally round in shape. Also, blood cells only deform by a biomechanically limited amount accounting for relatively small errors in their round shape. Thus, knowing that the 1D line scanner frequency is substantially consistent and that sweep time can be measured accurately (e.g. $<3.3 \times 10^{-5}$ seconds per sweep captured at a 30 kHz acquisition rate), the speed of objects that self-scan by traversing the 1D scan line can be measured. If the width of the cell (transverse width) is measured, and the apparent temporal width of the cell (temporal duration which a single cell is present in line scan), then the distance (width) per time (i.e. per n line scans) can be used to measure single cell blood velocity. In other words, the temporal elongation, or contraction as represented by the elongation ratio, defines the velocity of objects that self-scan by traversing the 1D scan line.

Roundness of Objects: The computer process can also optionally report a roundness metric. For example, the ratio of $2 \pi r/\pi r^2$ can provide a metric where objects with metrics close to 1 show high circularity (i.e. the perimeter is very well predicted by the radius).

Figure 10B:
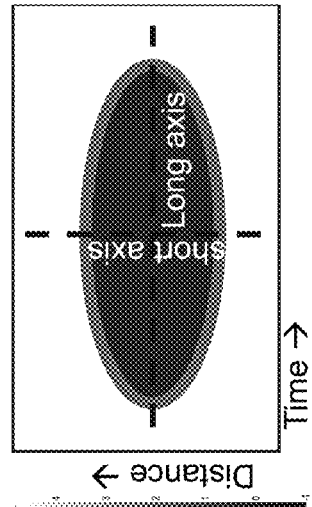
FIG. 10B shows an illustration of the velocity elongation principle.
Figure 10A:
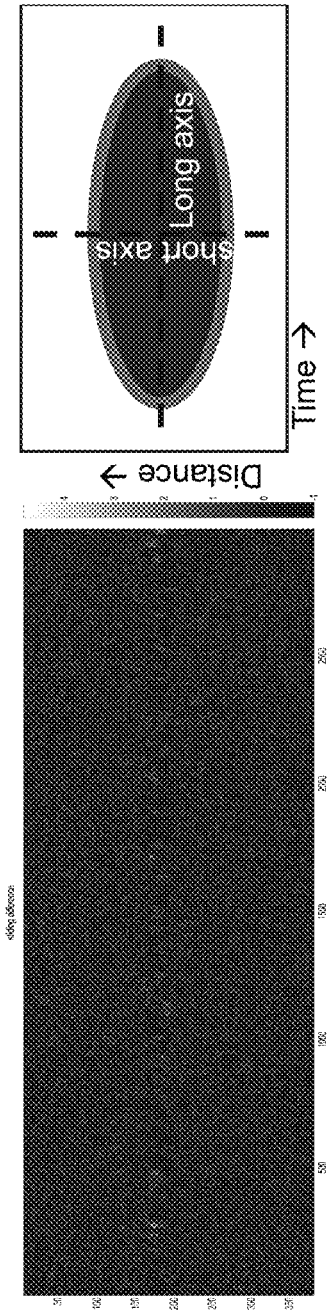
FIG. 10A shows a 1D successive line scan image.
Figure 10C:
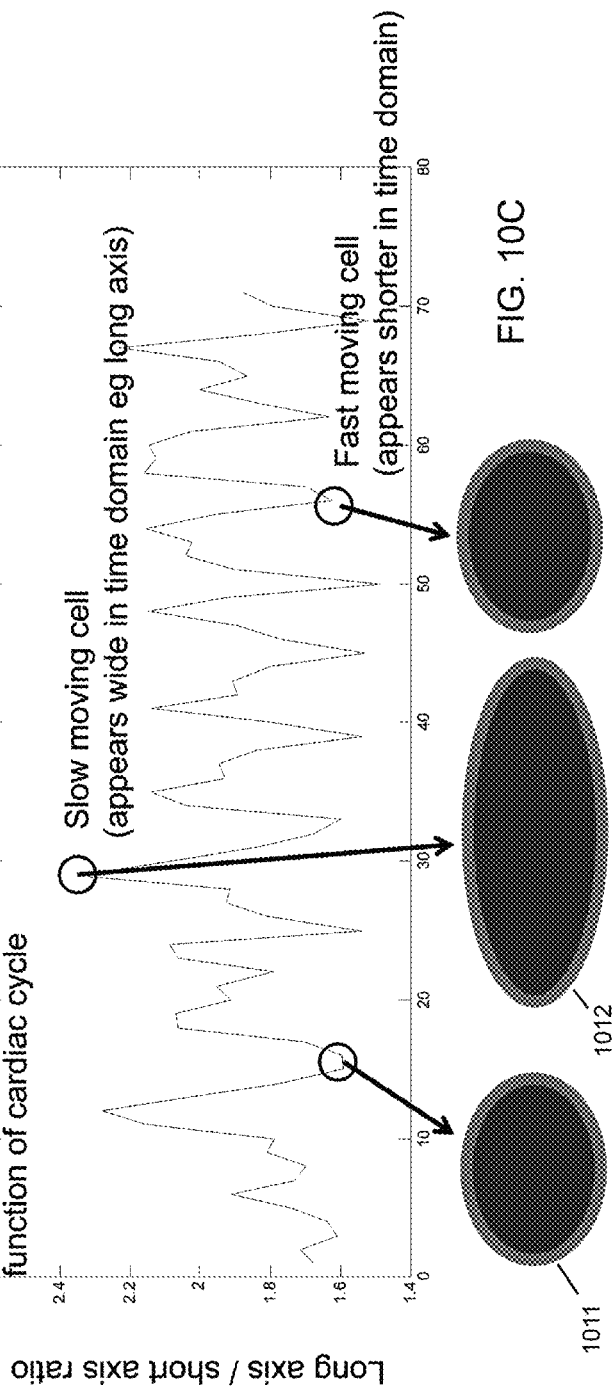
FIG. 10C shows a graph of elongation ratio for successive 1D scans and for several blood cells.

FIG. 10A shows a 1D successive line scan made according to the new techniques described hereinabove. A train of blood cells can be seen to be moving through a blood capillary. FIG. 10B shows an illustration of the elongation principle. The short axis of the representative blood cell falls along the 1D scan line and thus provides an accurate representation of physical length substantially independent of object velocity. However, the long axis provides a measurement of the elongation of the object and is directly related to the velocity of the object traveling through the blood capillary across the 1D scan line. FIG. 10C shows a graph of elongation ratio over time (successive 1D scans) and for several blood cells. The velocity measurement is sensitive enough to show changes in individual cell velocity over time related to the cardiac cycle. Below the graph of FIG. 10C a relatively less elongated illustration of a blood cell 1011 is shorter in the long axis and shows a corresponding lower long axis to short axis ratio. By contrast, a relatively more elongated illustration of a blood cell 1012 is longer on the long axis and shows a corresponding higher long axis to short axis ratio. In other words, a faster moving blood cell (e.g. blood cell 1011) appears shorter in the time domain.

In some embodiments, after cells have been identified, their properties can be averaged to increase signal to noise ratio of individual observations. FIG. 11A, FIG. 11B, FIG. 11C, FIG. 11D, FIG. 11E, show exemplary 1D successive line scanning images using the techniques described hereinabove. Several features of identified cells are shown in each image, including, for example, cell intensity polarity (dark cell or bright cell), and cell ratiometric width (long axis vs short axis, cell area vs dimensional axis). It is contemplated that such 1D successive line scanning image measurement techniques can be used to identify subclasses of cells (for example, to differentiate white blood cells and red blood cells).

Figure 11A:
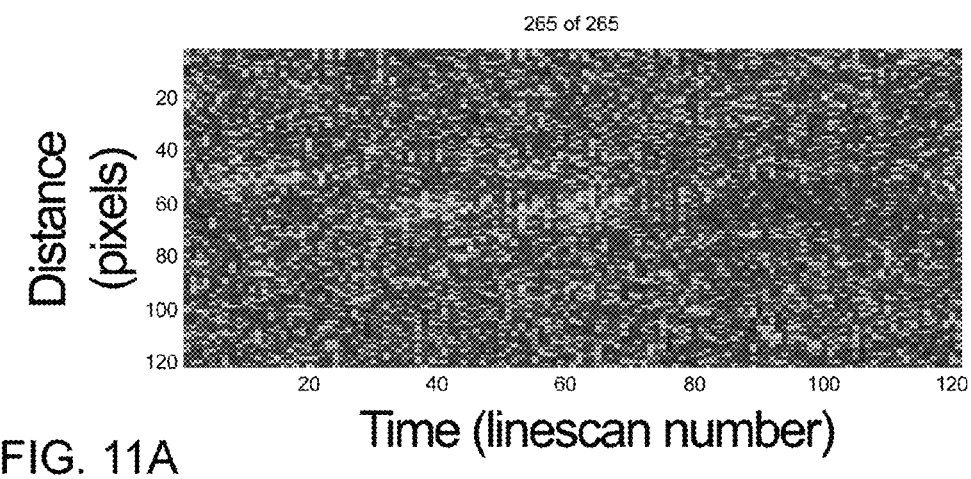
FIG. 11A shows a black and white representation of a 1D successive line scan image.
Figure 11B:
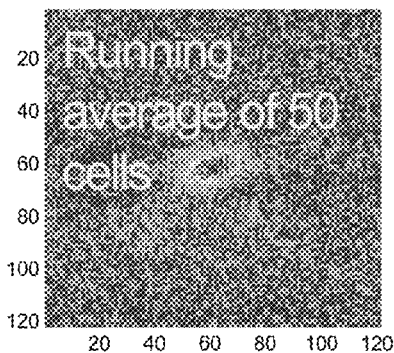
FIG. 11B shows a black and white representation of a 1D successive line scan color enhanced image running average of 50 blood cells.
Figure 11C:
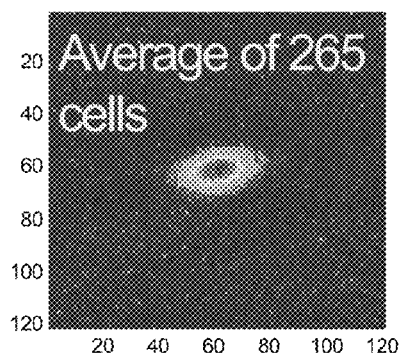
FIG. 11C shows black and white representation of a 1D successive line scan image running average of 265 blood cells.
Figure 11D:
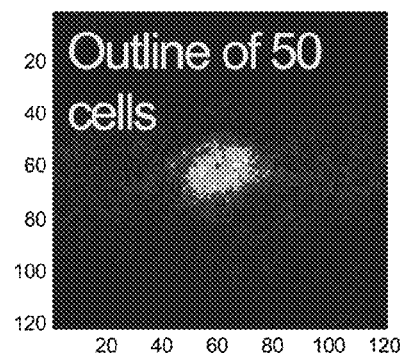
FIG. 11D shows black and white representation of a 1D successive line scan image of an average of the outline of 50 cells.
Figure 11E:
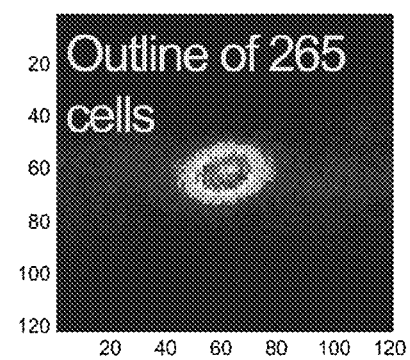
FIG. 11E shows black and white representation of a 1D successive line scan image of an average of the outline of 265 cells.

FIG. 11A shows a 1D successive line scan image. It is contemplated that for such line scan images, a positive contrast agent could used to enhance contrast. FIG. 11B shows a color enhanced running average of 50 blood cells useful for more accurately calculating the cell speed. FIG. 11C shows a running average of 265 blood cells, also useful for more accurately calculating the cell speed. FIG. 11D shows an average of the outline of 50 cells, and FIG. 11E shows a color enhanced distribution of the outline of 265 blood cells. Such enhanced distributions of cell outlines show a consistent object size, indicating a relative homogeneity of passing blood cell sizes.

It is contemplated that positive and/or negative contrast techniques can be used for observing the movement of an object in a blood vessel. For example, a positive contrast agent can be used to label an object, such as for example, a blood cell or a diagnostic object. Also, for example, using a negative contrast technique, an agent can be applied to, or administered to the matter surrounding an object of interest.

Figure 12C:
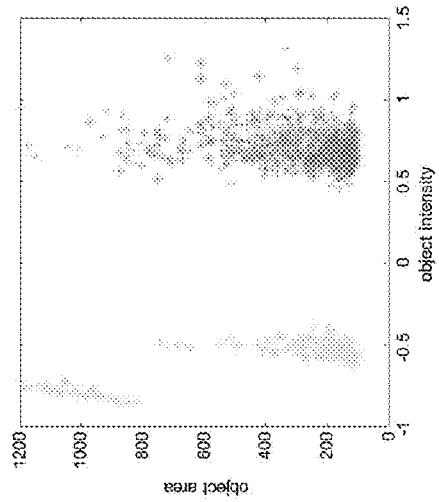
FIG. 12C shows a graph of object area plotted versus object intensity.
Figure 12B:
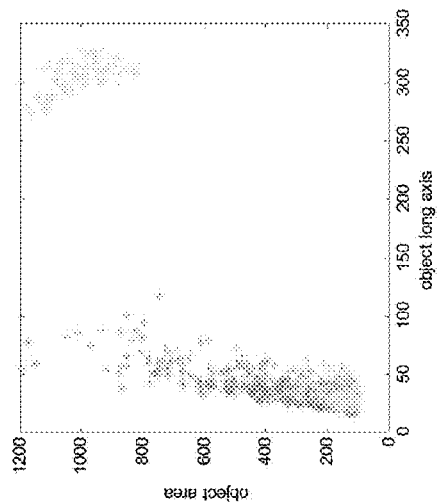
FIG. 12B shows a graph of object area plotted versus object long axis.
Figure 12A:
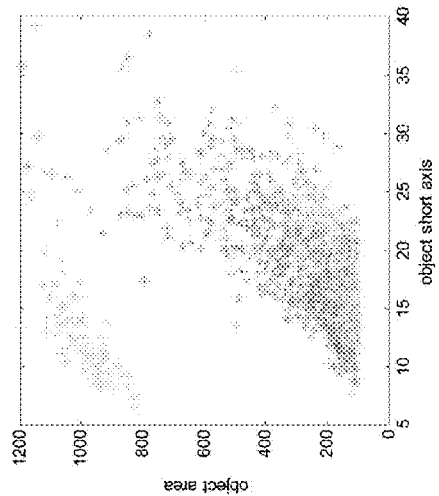
FIG. 12A shows a graph of object area plotted versus object short axis.
Figure 12F:
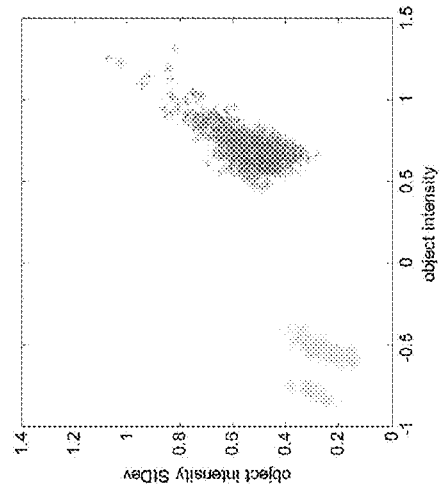
FIG. 12F shows a graph of object intensity standard deviation plotted versus object intensity.
Figure 12E:
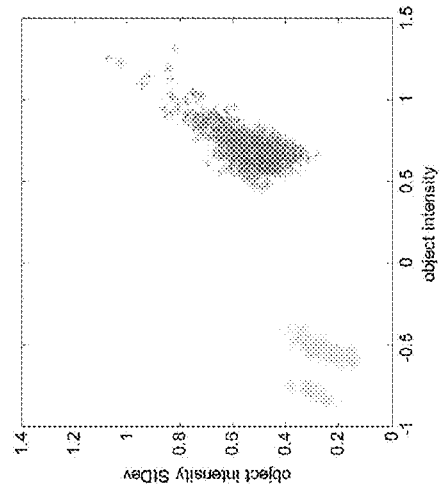
FIG. 12E shows a histogram of object area as a function of cell count.
Figure 12D:
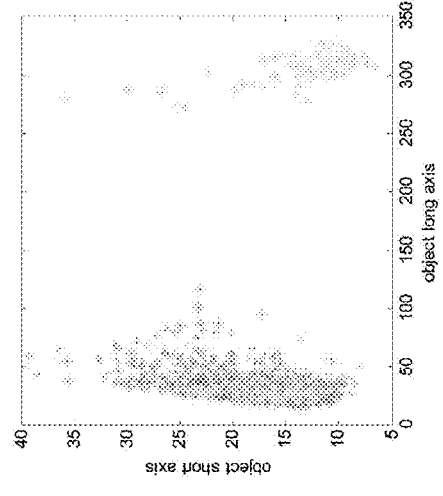
FIG. 12D shows a graph of object short axis plotted versus object long axis.

FIG. 12A to FIG. 12F show various exemplary graphical presentations which "cell classing" in the living eye based on 1D successive line scan images using the new techniques described hereinabove. Two populations of cells (light and dark data point marks) show different optical properties and shapes allowing for them to be classed based on multiple parameters. FIG. 12A shows a graph of object area plotted versus object short axis. FIG. 12B shows a graph of object area plotted versus object long axis. FIG. 12C shows a graph of object area plotted versus object intensity. FIG. 12D shows a graph of object short axis plotted versus object long axis. FIG. 12E shows a histogram of object area as a function of cell count. FIG. 12F shows a graph of object intensity standard deviation plotted versus object intensity. The ability to separate these populations enables cell classing. It is contemplated that parameter space in the future will report many other optical attributes unique to individual classes of cells.

Figure 13A:
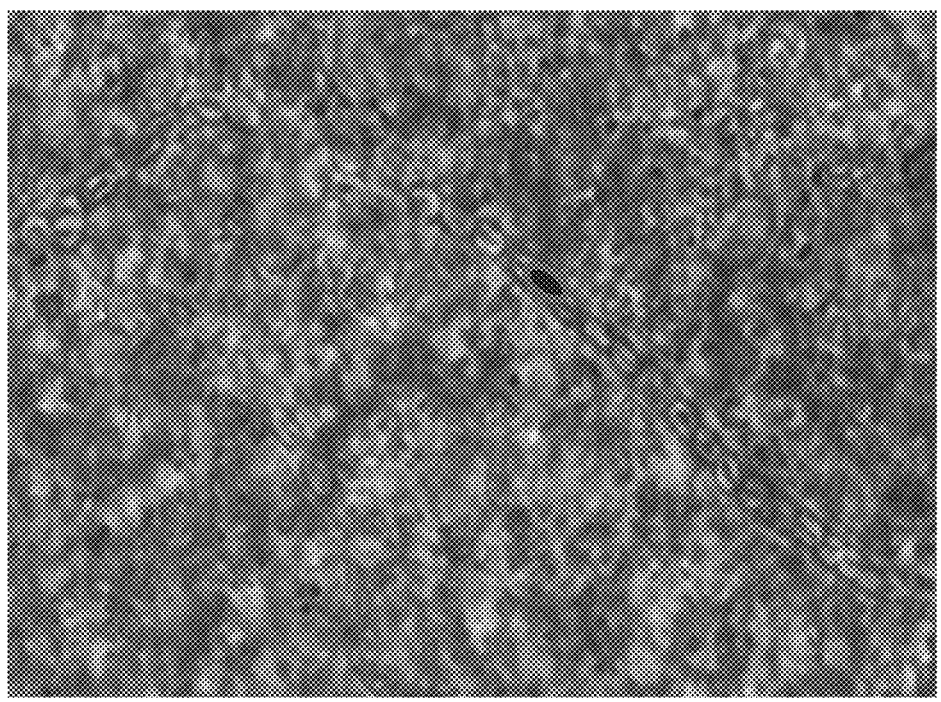
FIG. 13A shows a 2D image of a surface with blood capillaries.
Figure 13B:
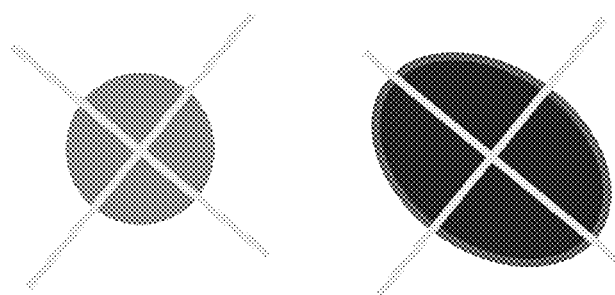
FIG. 13B shows a rounded cell shape on the left side compared with the heterogeneous strained cell shape on the right side.

FIG. 13A shows a traditional 2D image of a surface with blood capillaries that illustrates blood cells of different classes have different biomechanical strain characteristics. Cells of different classes can have different biomechanical strain characteristics, thus allowing for short-long axis identification. For example, the cell on the right side of FIG. 13B can be seen to have a heterogeneous strain (i.e. an ellipsoidal quotient greater or less than one compared to the cell on the left side of FIG. 13B).

Protection of In Vivo Imaged Surfaces: At some optical power levels and/or sweep speeds of point scanning instrumentation such as SLO or AOSLO, it there can be a risk of damage to cells on the 1D scan line. For example, there could be phototoxic accumulation (thermal or photochemical) at any one position on the 1D scan line. However, a sufficiently slow sweep of the (fast) line scan across a vessel which captures successive line scans at different positions along the vessel, can still record the same blood cells in transit through that vessel. For example, slowly moving the line scan in continuous or discrete steps (epochs), can substantially eliminate the risk of phototoxic accumulation (thermal or photochemical) at any one position. In some embodiments, it is contemplated that the position of the line scan can be moved once a maximum permissible exposure (MPE) or any other suitable pre-determined exposure limit or exposure threshold is reached at any given position. MPE can be determined, for example, by the applicable ANSI standards.

FIG. 14A shows one exemplary embodiment of a 1D successive line scan imaging approach to comply with optical power—time exposure concerns. For example, so as not to over-expose one particular location on a surface being imaged, there can be three different substantially fixed 1D lines as superimposed over the 2D image of FIG. 14A. Using the 1D successive line scan techniques described hereinabove, a spatio-time image can be developed from 1D successive line scans at each of the lines. Exemplary 1D successive line scan images are shown in FIG. 14B, FIG. 14C, and FIG. 14D which correspond respectively to 1D scan data acquired at each of the three exemplary 1D locations on the surface of FIG. 14A. The 1D successive line scan images are shown in FIG. 14B, FIG. 14C, and FIG. 14D were taken by moving from one substantially fixed 1D line to the next substantially fixed 1D line after a period of time, or following an "epoch" of time.

Figure 15A:
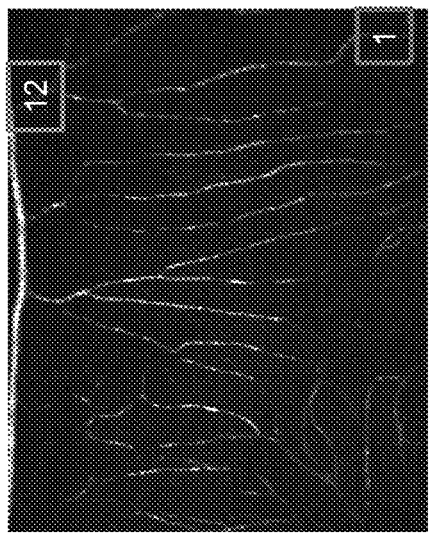
FIG. 15A shows a 2D image overlaid by two boxes labeled 1 and 12 respectively.
Figure 15B:
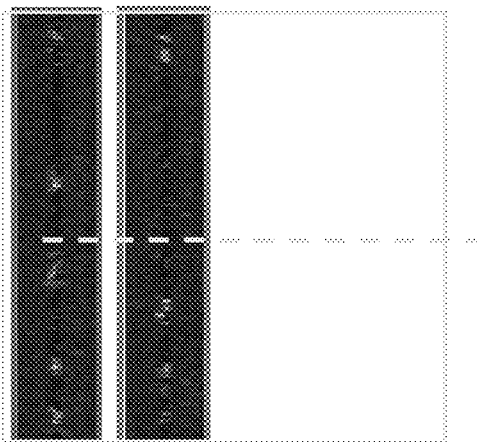
FIG. 15B shows two corresponding 1D successive line scan images for locations 1 and 12 on FIG. 15A.
Figure 15C:
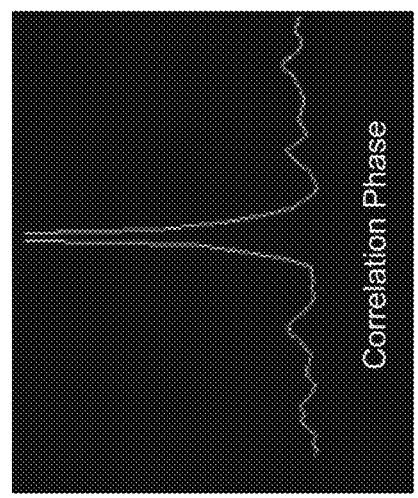
FIG. 15C shows an exemplary graph illustrating phase correlation.

Spatio-Temporal Cross Correlation: Two or more scanners can permit a spatio-temporal cross correlation useful to measure cell transit time. The measurement can be based on an optical train of events. FIG. 15A shows a traditional 2D image overlaid by two boxes labeled 1 and 12 respectively. In one exemplary embodiment, two scanners can be used to perform the spatio-temporal cross correlation method. FIG. 15B shows two corresponding 1D successive line scan images for locations 1 and 12 on FIG. 15A. A phase delay of the same pattern of vessels reveals blood transit time from two observers (e.g. FIG. 15A, FIG. 15B, point 1 and point 12). FIG. 15C shows an exemplary correlation phase graph demonstrating an identification of the same group of cells observed at location 1, later traversing location 12.

Figure 16A:
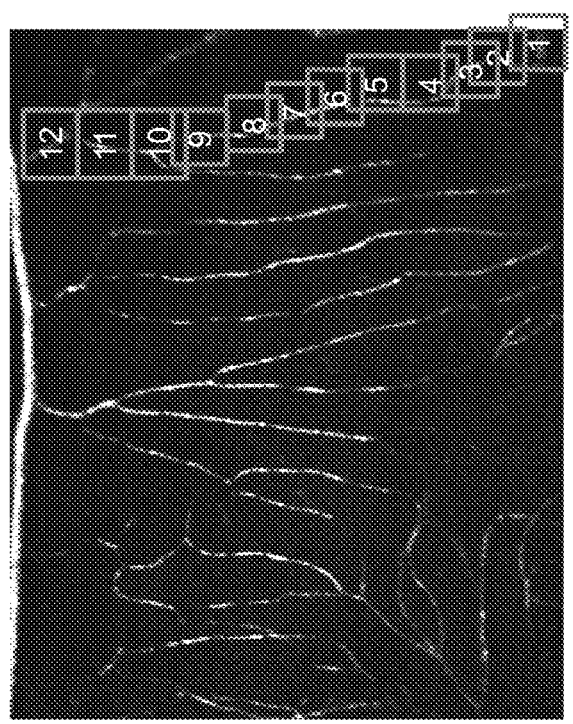
FIG. 16A shows a 2D image overlaid by 12 boxes labeled 1 to 12 respectively.
Figure 16B:
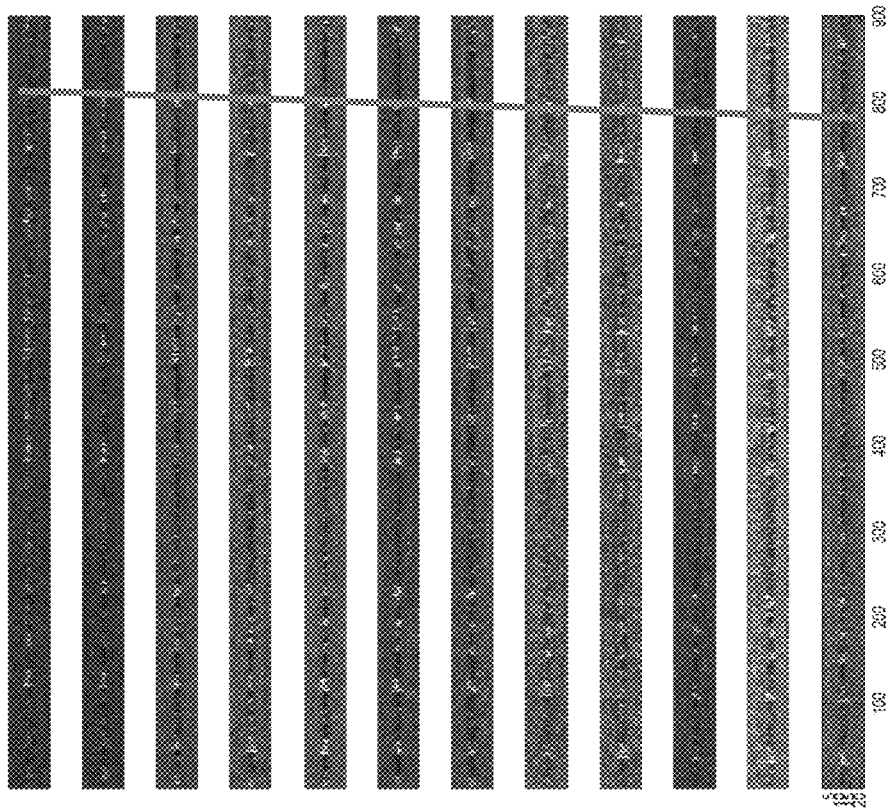
FIG. 16B shows 12 corresponding 1D successive line scan images for each of the 1D foot prints at the locations 1 to 12 of FIG. 16A.

FIG. 16A shows a traditional 2D image overlaid by 12 boxes labeled 1 to 12 respectively. In this exemplary embodiment, there can be multiple positional detectors which can identify a temporal lag or phase delay in blood cell trains, enabling velocity detection. For example, FIG. 16B shows 12 corresponding 1D successive line scan images for each of the 1D foot prints at the locations 1 to 12 of FIG. 16A. The vertical line shows a substantially simultaneous view of the 12 different footprints. Noting a presence or absence of an object in the blood cell along the 12 locations of the line at the same time can be used to produce a numerical code, which can be viewed in some embodiments as somewhat analogous to a Morse code, thus yielding an object in the blood vessel or "blood cell Morse code" to identify by one numerical indicator an "occupancy" and "occupancy distribution" of the blood vessel at any given time.

The 1D successive line scan techniques described hereinabove can also be used to measure multi-parametric information on the movement, shape, speed, and optical characteristics of single blood cells as they move in the living eye. In some embodiments a beam of light across scans blood vessels in the living eye at a fixed position. By scanning at a sufficiently high rate of speed, moving blood cells within vessels can be imaged in transverse section. Also, by scanning at a fixed position, the natural movement of blood cells across the fixed beam can produce an image of thousands-millions of blood cells that pass through the beam as a function of time. In some embodiments, the shape, internal structure, chromaticity, fluorescence, morphology, absorbance, transmittance, forward/backward/side-scatter, Mie scatter, Raman scatter, birefringence and/or other optical properties of moving blood cells can also be imaged allowing for complex cell-sorting and cell classification based on these features.

In addition to reporting cell structure, features and optical properties, the shape of an image made by use of the 1D successive line scan techniques described hereinabove can provide a way to calculate the velocity of the moving objects across the scan beam. Velocity calculations can be performed by measuring the elongation ratio of the object in the in the time axis relative to the known and fixed size of that particle as measured by its cross sectional dimension in the transverse scan direction. Circular and ellipsoidal objects that appear temporally stretched indicate slow moving cells, whereas temporally compressed objects are represented by fast moving cells. Calculating this "elongation ratio" provides a direct and objective way of reporting single cell speed based on known homogeneous morphology of blood cells and circulating foreign bodies.

In some embodiments, measurements can be enhanced by the known property that blood cells move in single file through microvessels and capillaries. Thus, there can be a one-by-one analysis of optical properties of a large population of cells as the blood cells flow past the illumination beam of the 1D scan line at high rates of speed. It is also contemplated that similar results can be achieved with high-resolution imaging instruments, especially those that use a scanned beam such as optical coherence tomography and adaptive optics and non-adaptive optics scanning laser ophthalmoscopes.

Prior to the 1D successive line scan techniques described hereinabove, the clinical state-of-the-art used fluorescent tracers to measure blood transit speed in the eye. Alternatively, other approaches use Doppler frequency shifts of moving particles to measure particle speed on average. By contrast, the new 1D successive line scan techniques strategy uses the natural optical properties of single blood cells to directly measure and report cell speed on a cell-by-cell basis yielding large data sets yielding classification and velocity detection of millions of cells non-invasively. Technology facilitating embodiments of the new techniques can use both high temporal resolution (acquisition rates >15 kHz) coupled with high spatial resolution (such as that captured with an adaptive optics scanning laser ophthalmoscope exceeding 1 micron spatial resolution).

The 1D successive line scan techniques offer improvements over the limitations of prior art in several respects. The 1D successive line scan techniques provide direct evidence of single blood cell speed rather than inferred speed (based on Doppler shift). The new techniques do not depend on the use of injectable fluorescent tracers in order to visualize single cells. The new techniques also provide exceptionally fast data acquisition (such as those used with fast scanners) to acquire data in the kilo Hz to Mega Hz temporal regime. Fast imaging provides large data sets of thousands of cells in short periods of time preempting the need for motion correction within the moving tissue bed (such as that in the living, moving retina). Measurements and reports of cell classification and velocity can be me made substantially in "real-time", forgoing need for post-processing and ex vivo evaluation of blood samples as is done in current phlebotomy and hematology. In this way, the device operates in ways similar to a flow cytometer (which to date, is a device that is used to classify cells ex vivo). Thus, the 1D successive line scan techniques can be used, for example, to provide fast retinal scanning thus effectively adding an in vivo flow cytometer function to an ophthalmoscope.

One major benefit of analysis based on the 1D successive line scan techniques is that the techniques can be used to observe the living body directly, rather than relying on ex vivo analysis. For example, the 1D successive line scan techniques can be used to measure the number of blood cells that transit a vessel per time indicating vessel health (e.g. vessel blockage/occlusion). The 1D successive line scan techniques can also be used to measure the shape of cells that pass the beam can report blood cell and systemic health (e.g. sickle cell disease diagnosis/follow up, hyperleukocytosis, systemic infection levels, metastatic particle detection). Another application for the 1D successive line scan techniques is to measure the morphology and size of cells can help categorize freely flowing subclasses of cells (e.g. the identification of number of red blood cells to white blood cells). Other applications include, imaging the circulation time and concentration of injected or endogenous tracers, and real-time imaging of drug and therapy interventions by analyzing blood content and circulating particles non-invasively and repeatability. When coupled with a real-time detection apparatus, the 1D successive line scan techniques can be used to modulate a laser in such a way as to temporally target and conduct photolysis of undesirable sub-cell classes such as, for example, malignant cells, circulating bacteria or other foreign bodies.

Applications: The 1D successive line scan techniques permit the investigation of single cell movement in the living body without the need for invasive blood draws. Using the intrinsic movement properties of single blood cells, the optical properties of cells can be characterized to provide information of the physiology of not only the blood cells, but also every tissue that the blood cells have interacted with. Because blood courses from the smallest capillaries in our retina to the major vessels of our largest organs, the blood carries with it important information about systemic health. Such information gathered by the 1D successive line scan techniques can be used to improve our understanding disease states, genetics, physiology and function of the normal living organism.

Specific applications for the 1D successive line scan techniques include the measurement of the chromaticity of blood cells which may provide information on hemoglobin oxygenation and cell classing (e.g., counting numbers of red and white blood cells per time or per volume). Also, variability in flow speed including diastolic and systolic velocity and velocity changes can be studied in response to physiological challenge can provide information cardiovascular health. Analysis of forward versus backward or side scatter from blood cells can be used for cell classification, enabling users to class large populations of circulating cells such as various sub-classes of white blood cells and red blood cells. While many of the exemplary applications described hereinabove relate to imaging of blood cells, the 1D successive line scan techniques also advantageously have an ability to image and track concentrations of injected particles (such as optically labeled drugs, microbeads and/or other small foreign bodies). It is contemplated that with advances in the resolution of the 1D successive line scan techniques, that there is a potential to image bacteria and circulating pathogens which have exceedingly small diameters, enabled by adaptive optics correction of distorted imaging wavefronts. It is contemplated that tracking and detection of malignant cells such as circulating bodies that may be metastatic in origin can be performed using 1D successive line scan techniques.

Another advantage of the 1D successive line scan technique is removing the need for injected contrast agents to visualize the flow of blood in the living eye. Therefore we can bypass the need for injecting potentially harmful contrast dyes which are typically needed to identify blood flow in the eye using techniques of the prior art. We have demonstrated using proof-of-concept methods, such as were described hereinabove, that the 1D successive line scan technique can be used to image, classify and track individual cells in addition to providing a new way to calculate blood cell speed. Moreover, by presuming blood cells are approximately round (especially as a population), we can calculate the deformation in the time domain to calculate blood speed. Because the frequency of linescan capture can be held substantially constant, we can count the number of times the same cell has been scanned by the laser beam based on its shape. Single cell velocity can be obtained by the equation:

$$\text{Single cell velocity} = \frac{\text{known cell diameter}}{(\text{number of line scans per cell}) \times (\text{time per line scan})}$$

a calculation which can be repeated for each cell. Because 1D successive line scanning techniques as described herein typically captures hundreds-through-millions of cells, the new technique enables population statistics of velocity and through averaging, greatly increases signal to noise ratio to accurately report velocity of average speed per time or per population. Such calculations can be facilitated by the remarkable homogeneity of blood cell size, especially the size of red blood cells which are typically ~6 micrometers in diameter. Even small deformations in cell diameter, the numerator term which may bias the results, can be overcome by having sufficiently fast acquisition which greatly weights the denominator term and enhances accuracy.

It is believed that the substantially real-time nature of 1D successive line scan techniques will provide a major benefit over current conventions for flow cytometry that are time consuming, costly and do not provide real-time data. For example, by eliminating the phlebotomist/hematologist's time for blood draws, no longer required, we now contemplate substantial real-time reporting of cell classification. In comparison, the current state of the art for similar measurement and analysis requires waiting for human input related to blood draw, blood centrifugation, plating, analysis and report. The 1D successive line scan technique performs the analysis rapidly by computer and has the potential to report cell class and velocity in real time with data acquisition. The blood draw is no longer necessary.

While this new 1D successive line scan methodology was developed in high-resolution ophthalmic imaging, it can be easily applied to other optically accessible tissues such as skin, where blood can be imaged optically with low distortion and scatter. In ophthalmic imaging, we find the benefit of reporting velocity and cell classing in the eye because the eye is optically clear, with comparatively little scatter and absorption and/or transmission, other considerations to be considered for highly scattering tissue such as skin, the eye can be coupled with non-invasive ophthalmic assessment, the eye allows for single vessel identification and tracking, and the eye enables visualization of blood properties in the central nervous system which may be unique to that of other systemic organs such as skin.

As described hereinabove, exemplary 1D successive line scan techniques have been realized by using an adaptive optics scanning laser ophthalmoscope which provides sufficient resolution to directly image single blood cells as they move through the ocular fundus. The instrument provides spatial resolution exceeding (~1 micron laterally) and sufficient temporal resolution currently demonstrated with 15 kilohertz acquisition (30,000 samples per second). This has permitted direct investigation of the morphology and characteristics of hemodynamic movement in the smallest vascular branches of the body, the capillaries as well as the larger arterioles and venules which contain blood cells moving at substantially faster speed.

At present, 1D successive line scan techniques can accurately identify peak velocity, velocity variation due to cardiac cycle, direction of blood flow and ability to image and report reflectance, and fluorescence properties of single cells. Test data has been benchmarked in blood flow from three species, humans, macaque monkeys and mice. As described in detail hereinabove, data shows empirical evidence that single blood cells can be imaged and counted.

Imaging Apparatus: While 1D successive line scan technique has been realized in adaptive optics scanning laser ophthalmoscopy, 1D successive line scan technique can also be performed using other types of ophthalmic imaging instruments as well as imaging in other organs such as the brain, skin and internal organs that are optically accessible. Of these organs, the eye is an example of an ideal optical portal to perform in vivo flow cytometry because of the clear optical pathway in which we can directly image micro blood vessels with minimal scatter from deep tissue imaging and without needing invasive implanted optical paths (e.g. fiber optics) to probe sub-surface blood flow, especially in the brain.

While the 1D successive line scan technique described hereinabove have been largely developed using an adaptive optics scanning laser ophthalmoscope, its application can be applied to any rapid temporal acquisition detector. For example, optical coherence tomographers (OCT) currently use acquisition frequencies in the kHz to mHz regime allowing for rapid collection of cross sectional profiles (tomogram). It is contemplated that rapid acquisition of a stationary cross sectional scan (2D data often referred to as a B-scan) could allow for imaging of passing blood cell volume (cross sectional lateral width×cross sectional axial depth×(cell velocity/passing cell dwell time)).

Also, scanning laser ophthalmoscopes (SLO) (i.e. without the adaptive optics correction of AOSLO instruments) also can collect kHz-mHz regimes. While optical aberrations may blur the point-spread of the interrogation beam at the vessel of interest, cells on the order of 2-25 microns in size with sufficient spacing (sparsity) can also be detected without AO correction. It is contemplated that spectral information regarding size, shape, chromaticity, forward/backward/side scatter and fluorescence may be detected and not only coherence (as measured by OCT) can be obtained using either an AOSLO or SLO instrument. In some embodiments, when available, the optional adaptive movement (typically an adaptive mirror movement) of an AOSLO apparatus to correct for undesired movement (e.g. undesired eye motion) during imaging, may be preferred over a non-adaptive SLO apparatus.

Also, slit-based cameras, where a line (rather than a point source swept across an image in scanning techniques) also can provide an exceptionally fast acquisition rate. This approach positions a stationary line to be sampled by a line-scan array detector (typically and M×N array). Thus, it is contemplated that either a line-scan or "slit-camera" can provide a fast enough acquisition of a line of data to pride a 1D image, equivalent of the 1D successive line scan technique described hereinabove obtained by use of point scanning instruments (e.g. AOSLO and SLO instruments). Any suitable 1D imager or 1D slit camera apparatus such as an apparatus that includes any suitable M×N pixel imaging device can be used. Typically M is less than N.

In some embodiments it is contemplated that M could be close to N or even equal to N where the image is then averaged across M to produce about a single pixel wide output, or an output where M is smaller than N.

Single Point Imaging (e.g. 1 pixel×1 pixel): In some embodiments, the new techniques described hereinabove can be performed in the absence of a lateral scan. Instead of the 1D footprint of a 1D image, a single point of light can be focused on a vessel to collect even faster data acquisition. The benefit here is that data acquisition rates are pushed into the mHz regime (millions of samples per second). In such a successive point imaging method, the result of successive point images over time is a virtual 1D spatio-temporal image. Point scans or point images can be thus also be transformed into a virtual one dimensional (1D) or "1D like" successive time images (e.g. a virtual 1D spatio-temporal image).

A trade-off, however, is that one loses the lateral dimension meaning shape of cells may not be detected. This trade-off may be worthwhile in conditions where cell shape measurements are not important, but high temporal acquisition of fluorescence, forward-backward-side scatter, chromaticity and reflection properties are most important. With increased temporal acquisition in MHz regime, data may also be temporally averaged into a slower bandwidth (temporal binning), which increases signal-to-noise ratios which may serve to limit the sensitivity of the approach.

Fluorescence Tagging: Blood cells/plasma can be labeled with fluorescence to correlate observed moving bodies with confirmed fluorescence tagging. By validating the correlation of non-labeled cells with that of labeled cells, our work seeks to identify and classify circulating cells based on their intrinsic optical properties thereby eliminating the need for invasive fluorescent tracers for cell classing.

It is also contemplated that methods described herein can be applied to other imaging strategies in the eye including optical coherence tomography (which provides not only optical information in a single dimension across the scanned beam, but also reports circulating cell shape in depth), adaptive optics imaging, eye-tracking and stabilization which enables the scanned beam to be reliably stabilized on a vessel thereby minimizing motion and movement artifact. This approach can also be implemented in flood based illumination imaging strategies that use sufficiently fast CCD, CMOS or array detectors (e.g. M×N pixel integrated devices) by projecting a beam of light via a cylindrical lens on the ocular fundus which transects retinal vessels.

In general, it is contemplated that the methods described hereinabove can be integrated into any one of an array of scanning and point source imaging techniques that are used in the eye such as scanning laser ophthalmoscopy, optical coherence tomography, ultrasound, Doppler laser analysis and manifestations of these approaches in other biometrics devices used in other tissues.

In summary, blood flow cytometry traditionally requires a blood draw followed by a time consuming process that requires skilled human guidance. Many benefits could be realized if this analysis could be performed noninvasively, such as, for example, using the new techniques described herein of in vivo flow cytometer. The new in vivo flow cytometer can, for example, use an adaptive optics scanning light ophthalmoscope (AOSLO) to image, classify, count and report the velocity of thousands of blood cells in the living retina in times as fast as seconds or faster.

Figure 17:
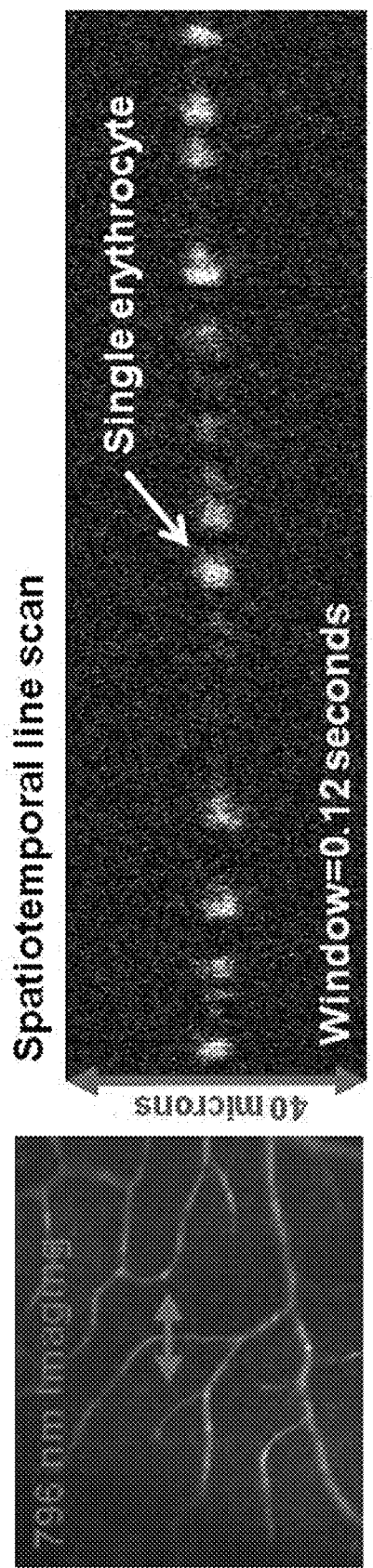
FIG. 17 shows another small area view to the left, and to the right another successive line scan image according to the new method.

For example, anesthetized mice were imaged with a two-channel AOSLO. One channel imaged capillaries in near infrared reflectance (NIR, 796 nm), a second imaged sodium fluorescein injected systemically (488-514 nm excitation, 534/25 nm emission). After AO correction, the slow scanner was stopped, allowing high speed line scans (30,000/second) perpendicular to a retinal vessel. Blood cells created a 2-dimensional spatio-temporal image as they move past the 1-dimensional scan. Data showed cell width and cell dwell time enabling calculation of cell velocity and reconstruction of cell shape as shown in FIG. 17. The centroid of each cell in NIR was used to register the fluorescence channel.

Figure 18:
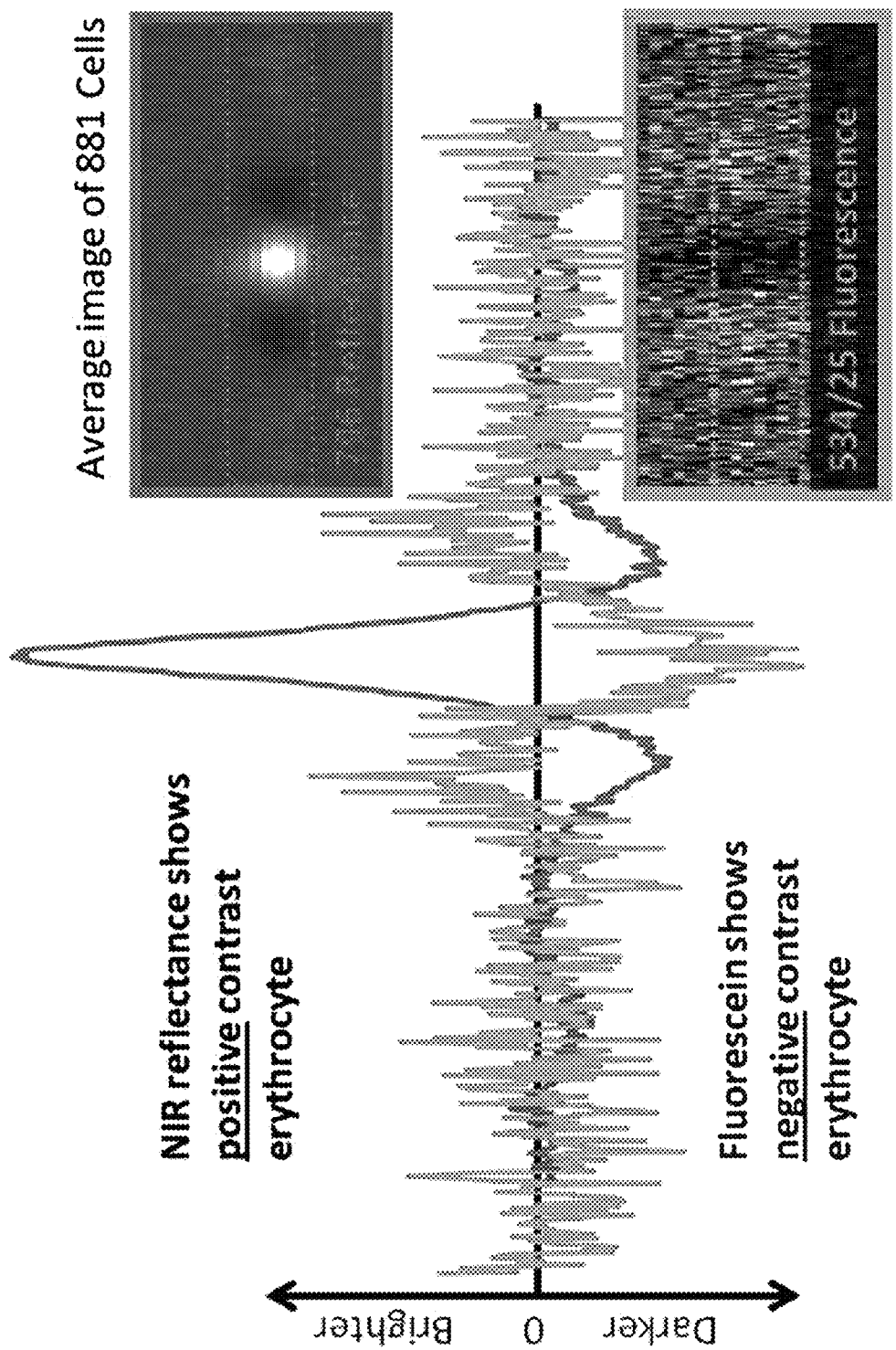
FIG. 18 shows a graph of simultaneous capture using negative and positive contrast with an illustration upper right of positive contrast with reflectance and an illustration lower right showing negative contrast.

Turning to the Results, Cytometry: We classified multiple cell populations based on cell shape, size, scatter and frequency of occurrence. When confocal imaging was focused on capillaries, AOSLO cytometry revealed thousands of putative erythrocytes and leukocytes that showed positive endogenous contrast. Unlike reflectance, fluorescence decreased when cells were present, a property of sodium fluorescein that preferentially labels plasma over erythrocytes as shown in FIG. 18. This provides evidence that positive contrast cells in NIR are red blood cells.

Velocimetry: It is contemplated that the in vivo cytometer could theoretically measure cell velocities >100 mm/sec in its current implementation (faster still in applications where data acquisition is faster), two orders of magnitude greater than the fastest blood cells in retinal capillaries. It is contemplated that such an approach could provide an absolute measure of blood velocity and variations corresponding to the cardiac diastolic and systolic cycle.

Therefore retinal flow cytometry can provide the first steps toward reducing the need for ex vivo blood analysis. This non-invasive strategy can count, classify and measure the speed of blood cells in vivo. Combined with fluorescein imaging, we provided the experimental evidence that positive contrast cells observed in the NIR represent red blood cells and not only white blood cells or aggregations of platelets.

The dwell time of each passing cell through the beam provides a new way to calculate absolute blood velocity. The exemplary 15 kHz acquisition rate also mitigated eye movement artifacts.

A light beam and detector can be used to measure optical properties of the flowing cells including optical scatter, fluorescence and cell chromaticity. Performing this analysis within the living organism provides great benefit that forgoes the need for blood culture and draw. Toward this end, we can use the eye as a transparent window to scan microvessels in the living eye with a modified adaptive optics camera to provide measures of blood cell count, morphology, fluorescence and velocity by harnessing the natural tendency for capillaries to provide a single stream of cells through a stationary scanned image beam. Using high-resolution adaptive optics to focus the interrogation beam in the living eye we analyze the optical properties of thousands of free circulating blood cells that cross the imaging linescan.

In exemplary experimental implementations, by averaging the centroid position of each identified cell in the NIR channel, we used the spatio-temporal position of the fluorescent channel to produce an average fluorescence image. When registering cells using sodium-fluorescein, we found that positive reflectance in the NIR channel produced a negative contrast image in the fluorescent channel. Presence of a positive contrast cell in the NIR channel led to a decrease in fluorescence, consistent with the property of fluorescein that labels plasma-albumin preferentially over white and red blood cells.

For example, this is different from negative contrast observed when imaging blood shadows at the photoreceptor layer. For example, trading spatial for temporal acquisition allowed for fast linescan capture, ~33 microseconds per acquisition. This rate enabled the ability to count the number of passing blood cells as they crossed the imaging beam.

In one embodiment, by use of the optical property of transverse and/or longitudinal chromatic aberration, two beams of light can be projected through the same optical device so as to be projected on different regions in the interrogation image (e.g. displaced on two separate locations on the retina). Using two or more beams of different wavelength, two independent line scans on the retina can be collected (imaged) which are spatially displaced either laterally (e.g. by transverse chromatic aberration) or in depth (e.g. by longitudinal aberration). By measuring or calculating the displacement of the spectrally different line scans, two or more channels of line scan data can be collected simultaneously without the need to move the beams by manual displacement of mirror angle. Calculating the spatio-temporal phase difference from two simultaneously measured line scans enables calculation of velocity by measuring the beam displacement and dividing by temporal phase shift of correlated data.

Figure 19:
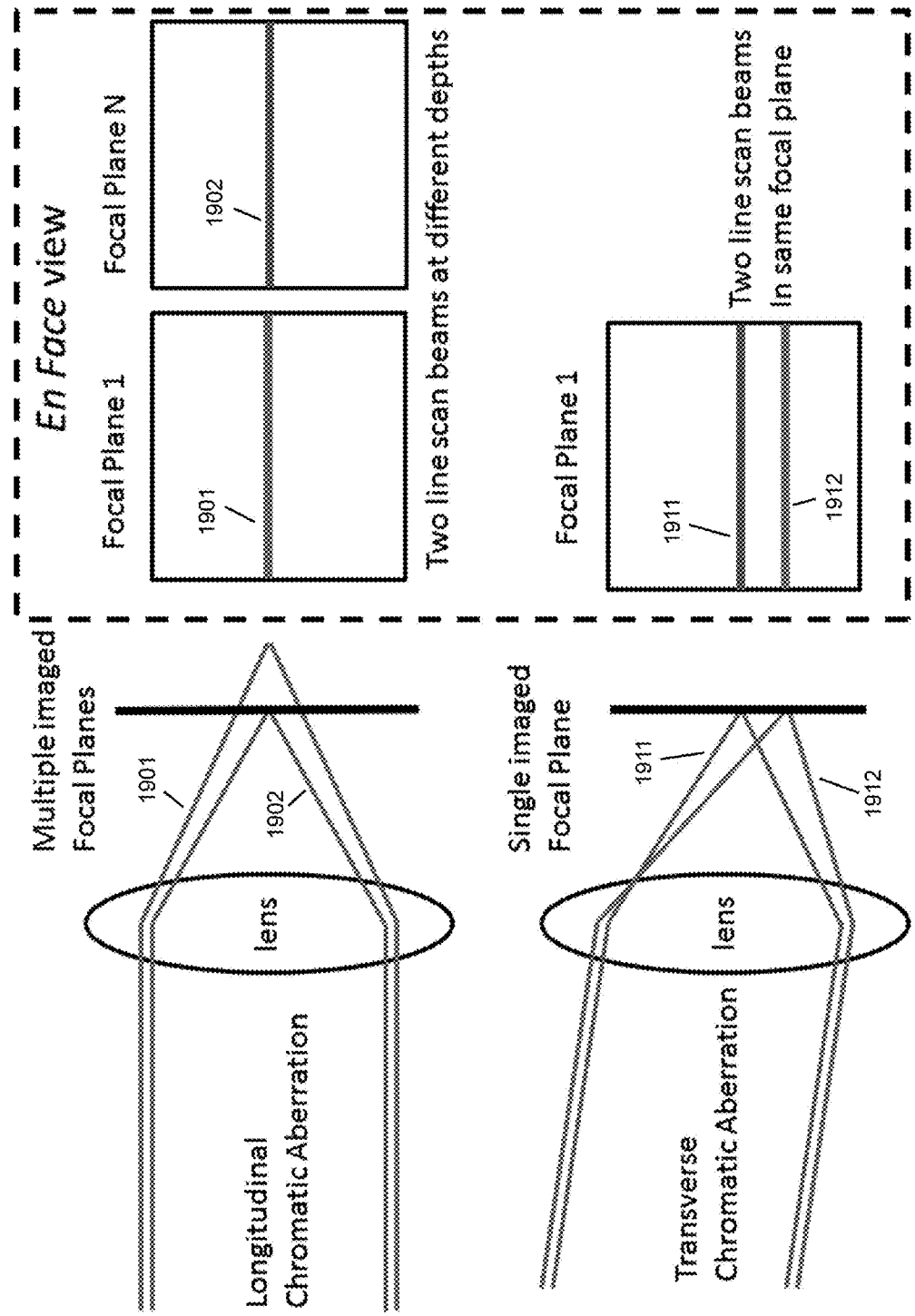
FIG. 19 shows an exemplary illustration of longitudinal and transverse chromatic aberration split line scan beams of different wavelength which project on different parts of the tissue of interest.

FIG. 19 shows longitudinal and transverse chromatic aberration split line scan beams of different wavelength to project on different parts of the tissue of interest. In longitudinal chromatic aberration (FIG. 19, top), two beams of different wavelength projected through the same optical apparatus are focused on different tissue layers. In transverse chromatic aberration (FIG. 19, bottom), two beams of different wavelength are projected through the same optical apparatus are focused on two adjacent regions in the same focal plane within the tissue.

Computer processes, such as firmware and/or software used to perform the techniques described hereinabove can be provided on any suitable computer readable non-transitory storage medium. Similarly, scan data can be written to any suitable computer readable non-transitory storage medium, typically a non-volatile computer storage media. A computer readable non-transitory storage medium as non-transitory data storage includes any data stored on any suitable media in a non-fleeting manner. Such data storage includes, for example, any suitable computer readable non-transitory storage medium, including, but not limited to hard drives, non-volatile RAM, SSD devices, CDs, DVDs, etc.

Displaying resultant images, such as images transformed from 1D line scanned images to virtual 2D images includes displaying the created images on any suitable display system, typically including a computer monitor. Displaying resultant images also includes any suitable type of printed image, such as printed or plotted images on a tangible media such as, for example, any suitable type of paper, plastic, or film.

Computer refers generally to any computer device. Any suitable computer can be used. For example, the computer can be microprocessor, microcomputer, microcontroller, or any suitable computer system embedded within an imaging system apparatus, or external to the imaging system apparatus. The computer can also be a conventional workstation, desktop, PC, LINUX or Apple operating system based computer, etc. It is also unimportant whether the computer is communicatively coupled to the imaging apparatus by any suitable wired or wireless communication method. Although, less likely, the computer can also be communicatively coupled to the imager system by a network such as a local network or the Internet. Image analysis or post-processing can also optionally be performed on another or different computer of any suitable type.

example: An AOSLO has been used to measure blood velocity in the living retina by tracking displacement of single blood cells. However, the complex morphology of blood cells has not yet been characterized due to insufficient cell boundary contrast. Differential imaging was used to resolve the shape of single red blood cells (RBCs) in the retinal circulation without using contrast agents.

Methods: Anesthetized C57BL/6J mice were imaged with an AOSLO using near infrared light. The confocal pinhole in the detection arm was replaced by a split-detector configuration [1,2] where the left and right half of the imaging point spread function was diverted into two, phase-locked photomultiplier tubes (PMT). Differencing the PMT signals provided differential contrast. Raster-scanning at 25 Hz was used to image slow moving RBCs. Point-scanning across a vessel at ~31 kHz provided high temporal resolution to image RBCs as they crossed the imaging beam.

Figure 20A:
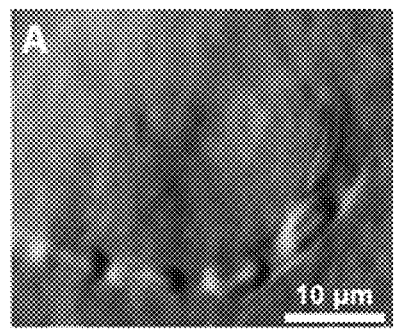
FIG. 20A shows an exemplary image of red blood cell (RBC) deformation as cells squeezed through capillaries.
Figure 20B:
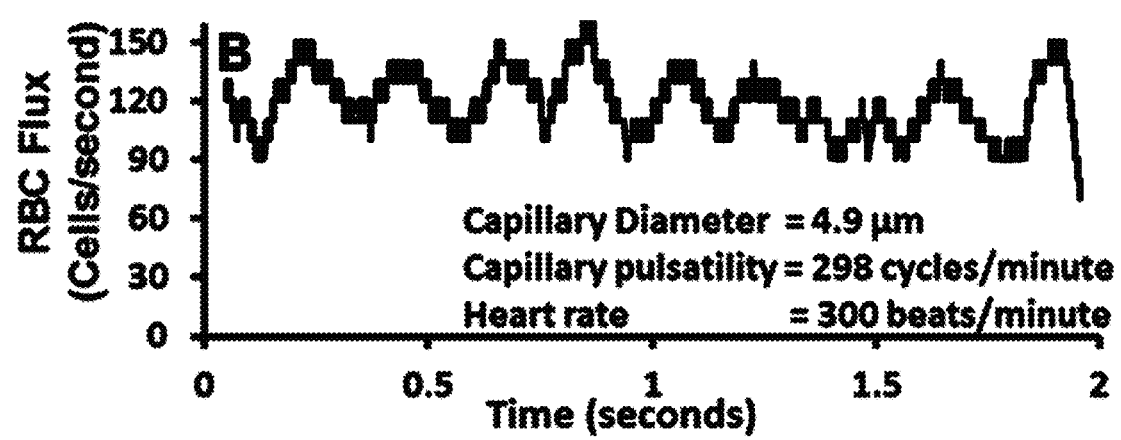
FIG. 20B shows a graph of RBC flux plotted over time.
Figure 21A:
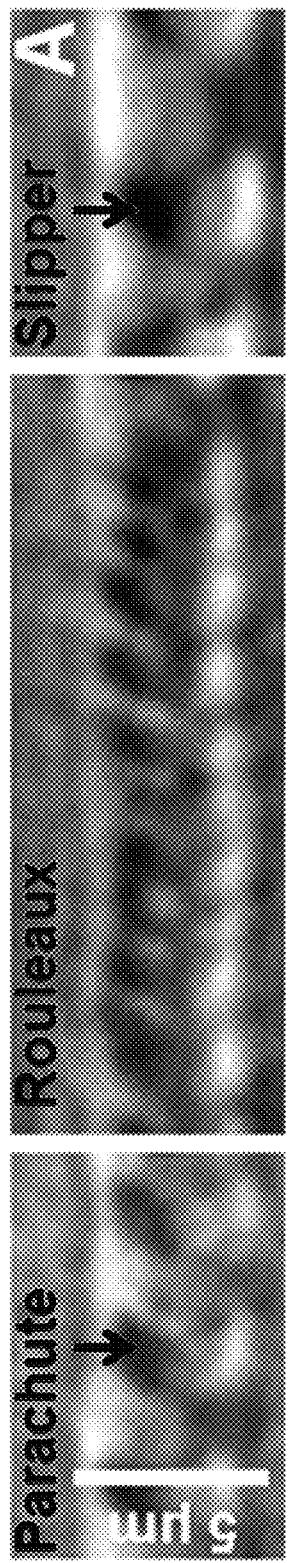
FIG. 21A shows exemplary images of parachute, rouleaux, and slipper morphologies.
Figure 21B:
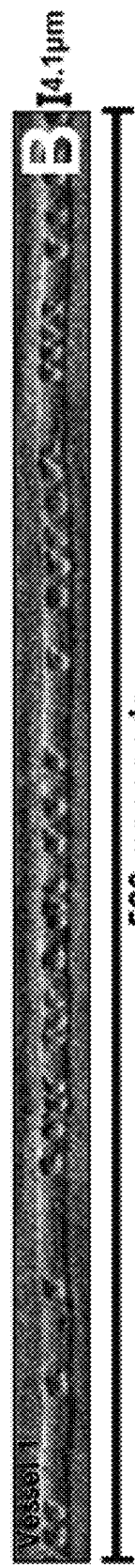
FIG. 21B shows an exemplary virtual 2D image of a capillary blood vessel.
Figure 21C:
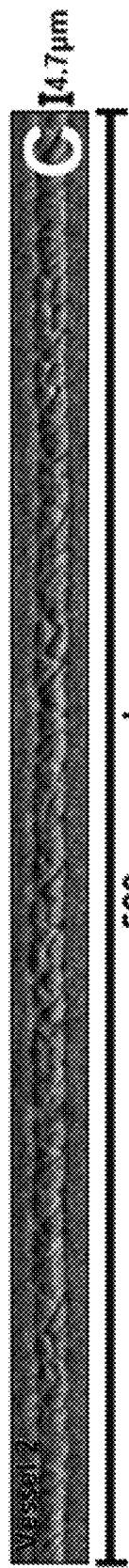
FIG. 21C shows an exemplary virtual 2D image of another capillary blood vessel.

Results: The morphology of RBCs was imaged using differential contrast enhancement. RBC deformation was absorbed as cells 6.5 µm in diameter squeezed through the ~4 µm vessel lumen in the smallest capillaries (FIG. 20A). RBCs maintained a biconcave surface despite a high deformation index (length/diameter) that ranged from 1.55-2.42, similar to those reported in other tissues. 31 kHz point-scanning across a vessel imaged a train of erythrocytes that could be counted (RBC flux). Capillaries ranged from 40-161 cells/s (RBC volume of 1.9-7.7 picoliters/s). Capillaries showed robust modulations in RBC flux that corresponded to the heart rate of the anesthetized mouse (~300 beats/minute) demonstrating that pulsatile flow is pervasive in the smallest vessels (FIG. 20B). The leading and trailing edge of moving RBCs displayed classic "parachute" and "slipper" morphologies (FIG. 21A) revealing the microscopic rheology of RBC interactions with the vascular endothelium, plasma and glycocalyx. Capillaries showed heterogeneity in RBC packing density despite having similar velocity and size (FIG. 21B, FIG. 21C).

Conclusions: The morphology, rheology, density and flux of single RBCs were imaged with AOSLO differential imaging. This near infrared approach provides new hemodynamic information in capillaries while mitigating phototoxic exposure and obviating the need for blood contrast agents that may alter hemodynamics. Future studies analyzing the shape of moving RBCs have the potential to provide differential diagnosis in a variety of systemic diseases without requiring a blood draw.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

REFERENCES

1. Scoles D, et al., In Vivo Imaging of Human Cone Photoreceptor Inner Segments. Investigative Ophthalmology & Visual Science, 55(7): 4244-4251, 2014.
2. Sulai Y N, Scoles D, Harvey Z, Dubra, A Visualization of retinal vascular structure and perfusion with a nonconfocal adaptive optics scanning light ophthalmoscope. Journal of the Optical Society of America A, 31(3): 569-579, 2014.

What is claimed is:

1. A method for creating a virtual 2D image of a single object moving in a blood vessel to determine a velocity of said single object comprising the steps of:
    acquiring multiple 1D images across a blood vessel disposed about adjacent to a substantially fixed footprint on a surface of an organ over a period of time by use of an adaptive optics scanning light ophthalmoscope (AOSLO) or a scanning light ophthalmoscope (SLO) imaging apparatus capable of acquiring 1D images, said substantially fixed footprint defining a line disposed in a plane about parallel to the surface of the organ, said line in said plane about perpendicular to the blood vessel, said imaging apparatus communicatively coupled to a computer;
    combining by computer said multiple 1D images to form a virtual 2D image showing said single object moving in said blood vessel;
    determining a velocity of a single object moving in said blood vessel from said virtual 2D image by said computer using an elongation ratio based on a known physical width of said single object and a distance as a single object width per time as determined from a subset of said multiple 1D images; and
    wherein a first axis of said single object falls along a 1D scan line to provide a representation of a physical length which is substantially independent of single object velocity and a second axis of said single object in said virtual 2D image provides a measurement of an elongation of the object which is directly related to the velocity of the object traveling through the blood vessel across said 1D scan line.

2. The method of claim 1, further including repeating said step of determining a velocity of an object moving in said blood vessel from said virtual 2D image for additional single objects.

3. The method of claim 1, wherein said method is repeated at two or more different substantially fixed 1D footprints so as not to exceed a pre-determined exposure limit.

4. The method of claim 1, further comprising one or more additional imagers and wherein said step of acquiring multiple 1D images comprises acquiring multiple 1D images simultaneously from multiple imagers over a period of time of said substantially fixed footprint on said surface of said organ and said step of combining by computer comprises combining by computer said multiple 1D images from said multiple imagers to identify a type of object of said single object.

5. The method of claim 1, further comprising one or more additional imagers and wherein said step of acquiring multiple 1D images comprises acquiring multiple 1D images from multiple imagers over a period of time, of two or more substantially fixed footprints on said surface of said organ, and said step of combining by computer comprises combining by computer said multiple 1D images from said two or more substantially fixed footprints on said surface of said organ to form two or more virtual 2D images showing said single object moving in said blood vessel.

6. The method of claim 5, further comprising after said step of combining by computer said multiple 1D images, performing a spatio-temporal cross correlation between at least two of said two or more virtual 2D images.

7. The system of claim 1, wherein said system is configured such that light returned from said substantially fixed location on said surface is directed to a detector selected from the group consisting of fluorescence, long wavelength, mid wavelength, short wavelength, forward scatter, back scatter and birefringence, and wherein said adaptive optics scanning light ophthalmoscope (AOSLO) or said scanning light ophthalmoscope (SLO) comprises at least one beam splitter configured to direct light returned from said substantially fixed location on said surface simultaneously to two or more detectors to provide a real-time cell class detection apparatus, and further comprising the step of determining an object type from a single measurement or from simultaneous measurements made by at least two different detectors.

8. The method of claim 7, further comprising a real-time cell class detection apparatus, wherein successive 1D line scan techniques are used to modulate a laser in such a way as to temporally target and conduct photolysis of undesirable classes.

9. The method of claim 8, wherein said undesirable classes comprise a sub-cell class selected from the group consisting of malignant cells, bacteria, and foreign bodies.

* * * * *